United States Patent
Gilot et al.

(10) Patent No.: US 10,287,633 B2
(45) Date of Patent: May 14, 2019

(54) TYRP1, A NATURAL MIRNA SPONGE, AND ITS USE IN MANAGING HUMAN MELANOMA AGGRESSIVENESS

(71) Applicants: UNIVERSITE DE RENNES 1, Rennes (FR); CENTRE NATIONAL DE LA RECHERCHE SCIENTIFIQUE—CNRS-, Paris (FR); CENTRE HOSPITALIER UNIVERSITAIRE PONTCHAILLOU, Rennes (FR)

(72) Inventors: David Gilot, Goven (FR); Marie-Dominique Galibert, Rennes (FR); Ghanem Ghanem, Drogenbos (BE); Fabrice Journe, Blaregnies (BE)

(73) Assignees: UNIVERSITE DE RENNES 1, Rennes (FR); CENTRE NATIONAL DE LA RECHERCHE SCIENTIFIQUE, Paris (FR); CENTRE HOSPITALIER UNIVERSITAIRE PONTCHAILLOU, Rennes (FR)

( * ) Notice: Subject to any disclaimer, the term of this patent is extended or adjusted under 35 U.S.C. 154(b) by 32 days.

(21) Appl. No.: 15/034,262

(22) PCT Filed: Nov. 6, 2014

(86) PCT No.: PCT/EP2014/073961
§ 371 (c)(1),
(2) Date: May 4, 2016

(87) PCT Pub. No.: WO2015/067710
PCT Pub. Date: May 14, 2015

(65) Prior Publication Data
US 2016/0265063 A1    Sep. 15, 2016

(30) Foreign Application Priority Data
Nov. 6, 2013 (EP) .................................. 13306524

(51) Int. Cl.
*A61K 48/00* (2006.01)
*C12Q 1/6886* (2018.01)
*C12N 15/113* (2010.01)

(52) U.S. Cl.
CPC ........ *C12Q 1/6886* (2013.01); *C12N 15/1137* (2013.01); *C12N 15/1138* (2013.01); *C12N 2310/141* (2013.01); *C12N 2320/30* (2013.01); *C12Q 2600/106* (2013.01); *C12Q 2600/156* (2013.01); *C12Q 2600/158* (2013.01); *C12Q 2600/172* (2013.01); *C12Q 2600/178* (2013.01); *C12Y 114/18* (2013.01)

(58) Field of Classification Search
CPC .................................................... A61K 48/00
See application file for complete search history.

(56) References Cited

U.S. PATENT DOCUMENTS 6,573,050 B1    6/2003   Ben-David et al.

FOREIGN PATENT DOCUMENTS

| EP | 1842916 A1 | 10/2007 |
|---|---|---|
| WO | 96/40249 A1 | 12/1996 |
| WO | 2004/043387 A2 | 5/2004 |
| WO | 2012082821 A2 | 6/2012 |
| WO | 2012/154935 A1 | 11/2012 |
| WO | 067710 A2 | 5/2015 |

OTHER PUBLICATIONS

PCT, International Search Report, Application No. PCT/EP2014/073961, dated Nov. 6, 2014, 8 pages.
PCT, Written Opinion of the International Searching Authority, Application No. PCT/EP2014/073961, dated Jun. 11, 2014, 12 pages.
D Yang et al: "RasGRP3. a Ras activator, contributes to signaling and the tumorigenic phenotype in human melanoma", Oncogene, vol. 30. No. 45. May 23, 2011, pp. 4590-4600. XP055104319.
Lauretta Levati et al: "MicroRNA-155 targets the SKI gene in human melanoma cell lines", Pigment Cell & Melanoma Research, vol. 24. No. 3, Jun. 5, 2011, pp. 538-550. XP055104331. (Abstract).
Jingjing Li et al: "Evidence for Positive Selection on a Number of MicroRNA Regulatory Interactions during Recent Human Evolution", PLOS GENETICS, vol. 8. No. 3. Mar. 22, 2012, p. e1002578, XP055104043.
F Journe et al: "TYRP1 mRNA expression in melanoma metastases correlates with clinical outcome", British Journal of Cancer, vol. 105. No. 11, Nov. 1, 2011, pp. 1726-1732, XP055104058.
Jos B. Poell et al: "A Functional Screen Identifies Specific MicroRNAs Capable of Inhibiting Human Melanoma Cell Viability", PLOS ONE, vol. 7, No. 8, Jan. 1, 2012, pp. e43569-e43569, XP055056889.
Kimberley A. Beaumont et al: "The Recycling Endosome Protein Rab17 Regulates Melanocytic Filopodia Formation and Melanosome Trafficking", Traffic, vol. 12, No. 5, Feb. 25, 2011, pp. 627-643, XP055110440.
Gilot et al., "A non-coding function of TYRP1 mRNA promotes melanoma growth", Nature Cell Biology, vol. 9, No. 11, Nov. 2017, 24 pages.

*Primary Examiner* — Kimberly Chong
(74) *Attorney, Agent, or Firm* — McAndrews, Held & Malloy, Ltd.

(57) ABSTRACT

The present invention relates to methods and reagents for the treatment of melanoma and/or of metastatic melanoma that directly or indirectly target TYRP1 RNA transcript. The invention also relates to methods for predicting if a melanoma patient will be therapeutically responsive to such methods of treatment and reagents, and to methods for assessing the effectiveness of such methods of treatment and reagents. The invention further relates to a combination of biological markers that allows the prediction of melanoma patients' survival irrespective of the treatment administered.

3 Claims, 15 Drawing Sheets
Specification includes a Sequence Listing.

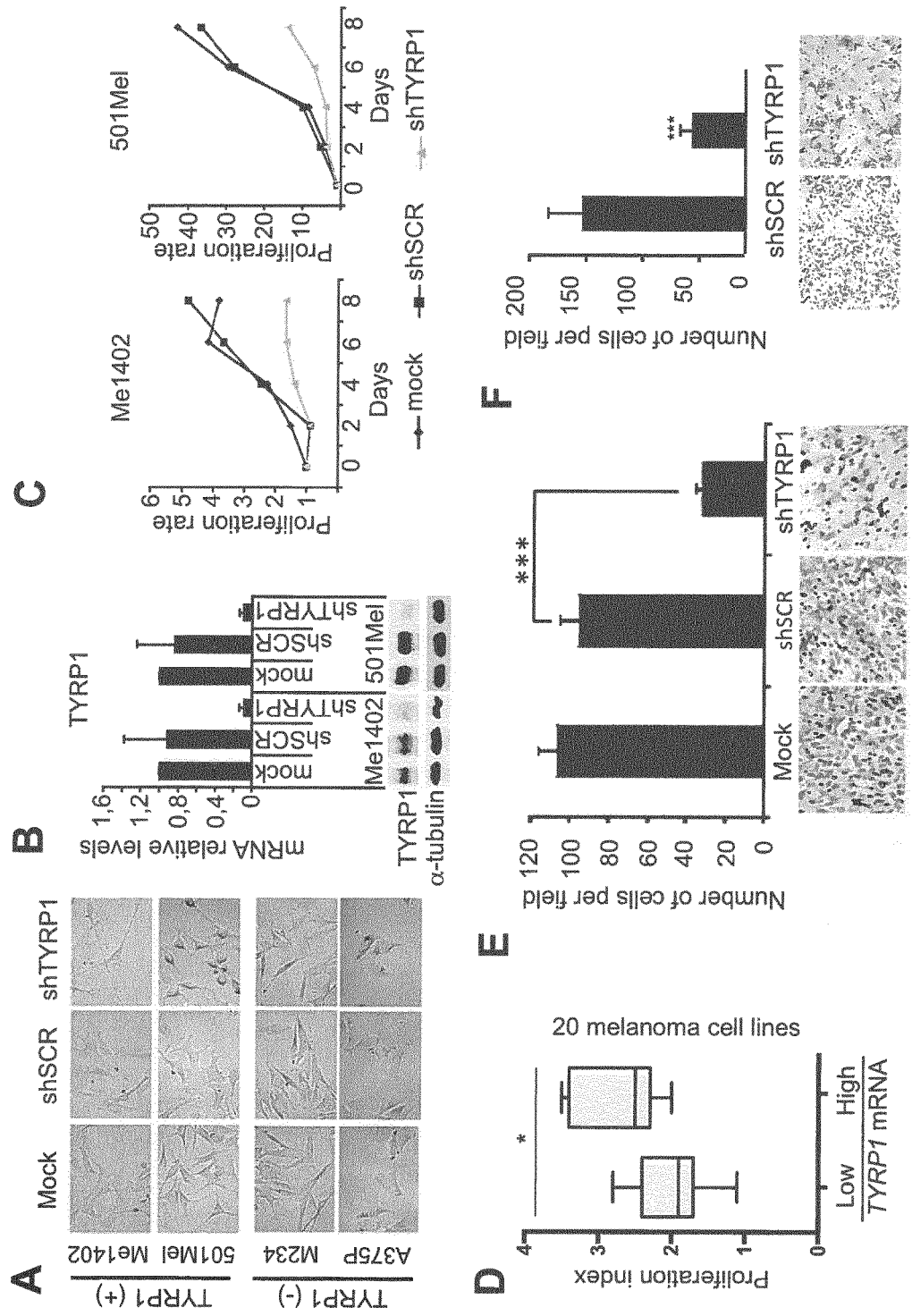
Figure 1(A)-(F)

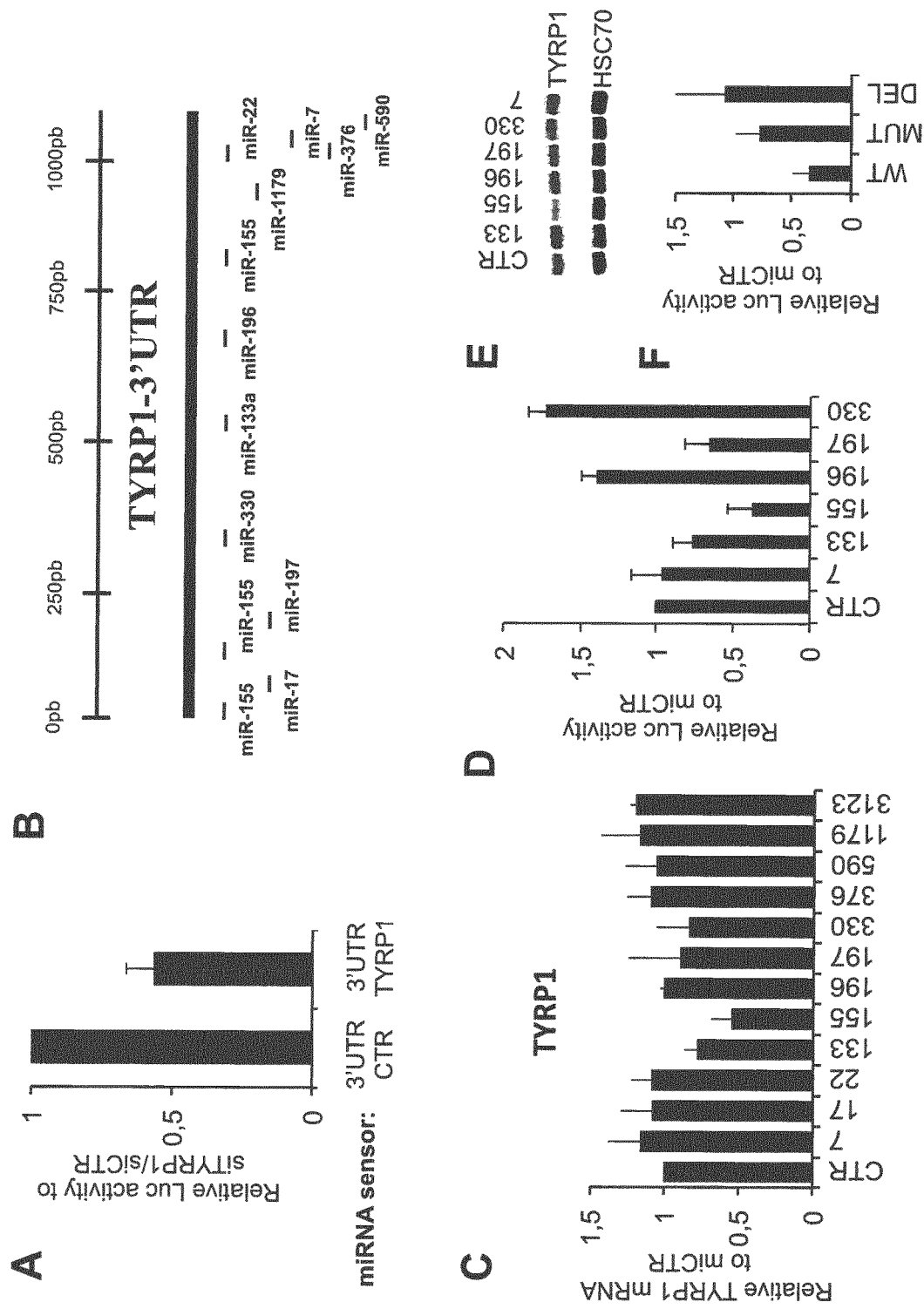
Figure 2(A)-(F)

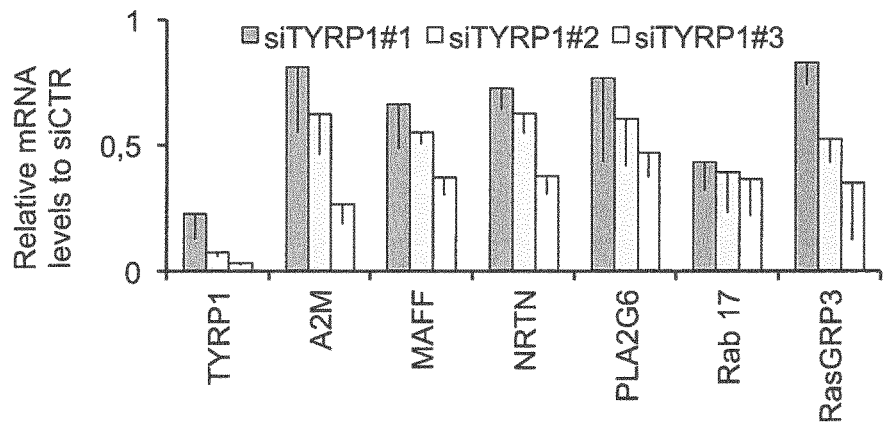
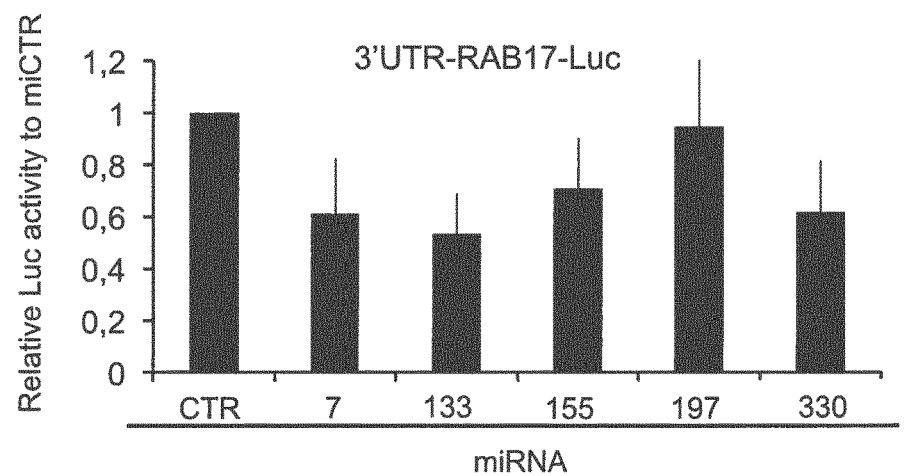
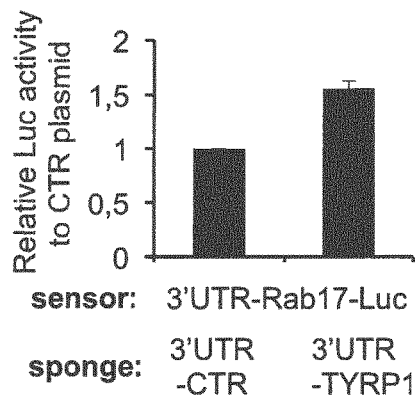
Figure 4(A)-(C)-(E)

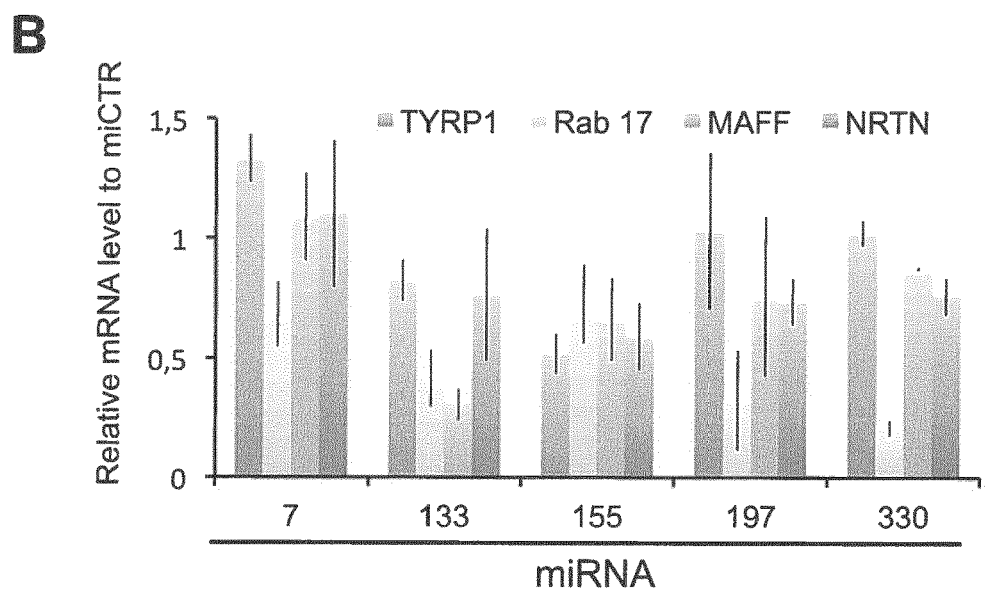
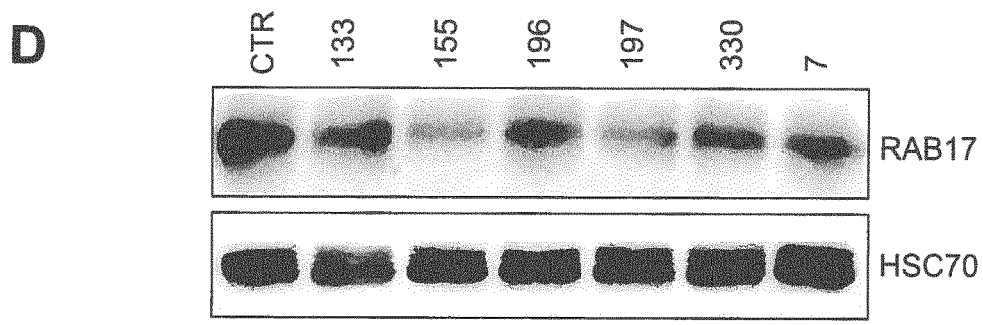
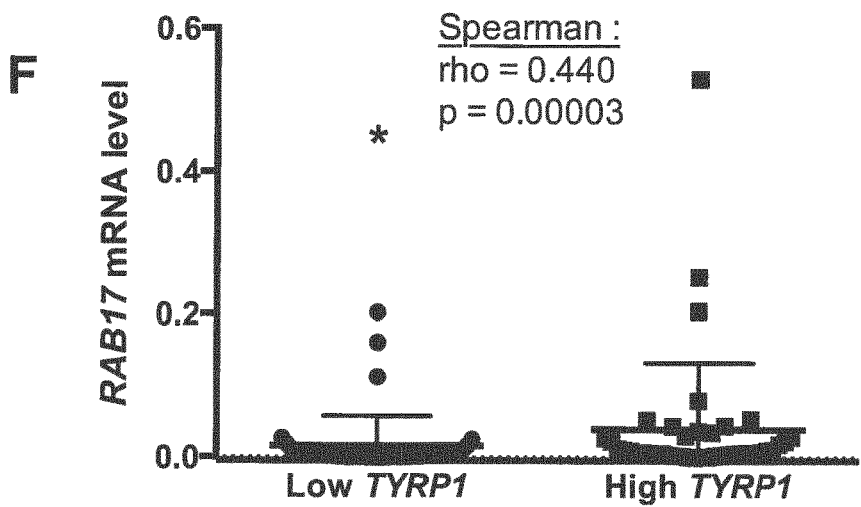
Figure 4(B)-(D)-(F)

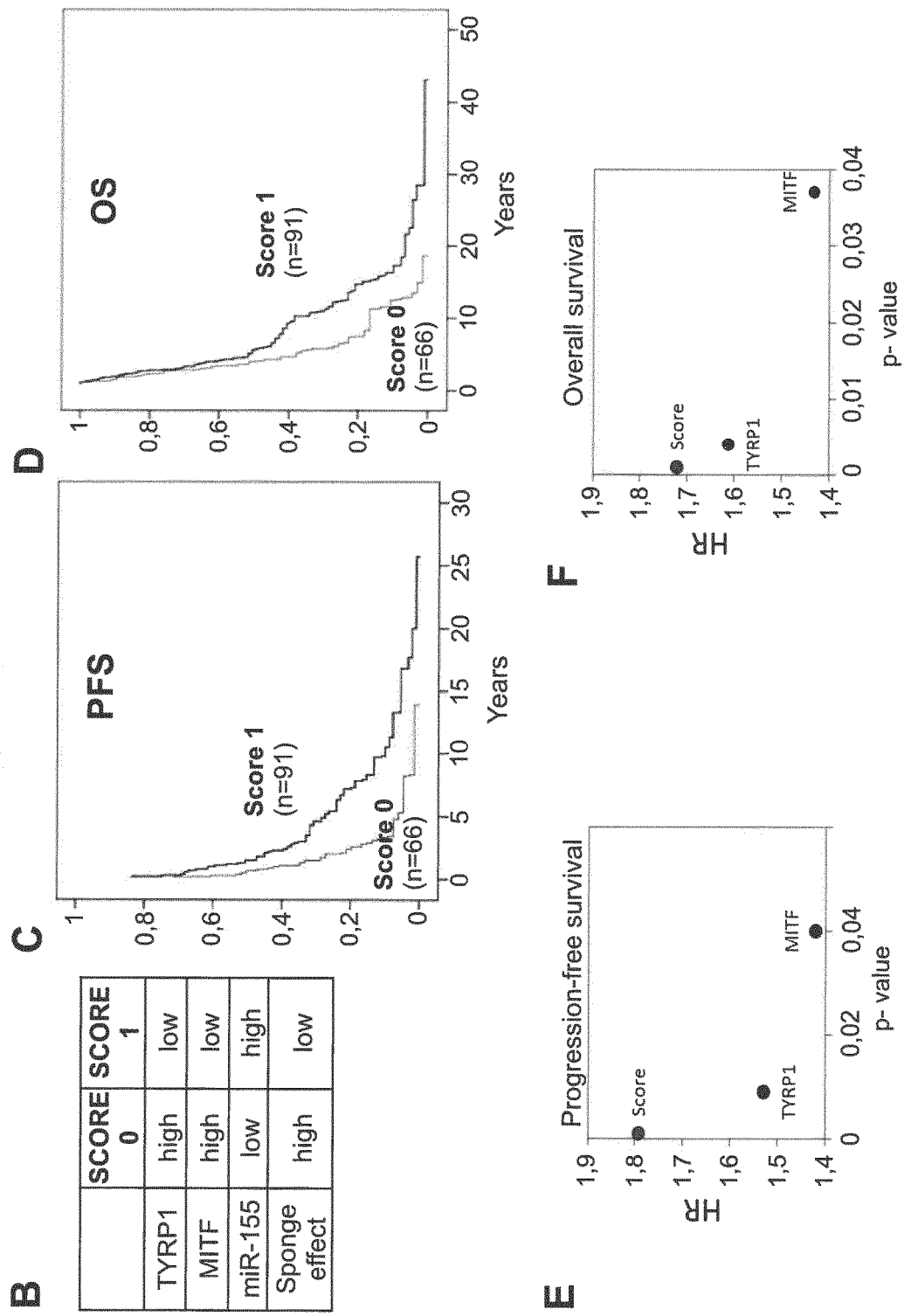
Figure 7(B)-(F)

TYRP1, A NATURAL MIRNA SPONGE, AND ITS USE IN MANAGING HUMAN MELANOMA AGGRESSIVENESS

RELATED PATENT APPLICATIONS

The present patent application is filed pursuant to 35 U.S.C. § 371 as a U.S. National Phase application of International Patent Application No. PCT/EP2014/073961, which was filed on Nov. 6, 2014, claiming the benefit of priority to European Patent Application No. 13 306 524.3 filed on Nov. 6, 2013. The content of each of the aforementioned patent applications is incorporated herein by reference in its entirety.

BACKGROUND OF THE INVENTION

Melanoma is a serious form of skin cancer often metastasizing to vital organs and other tissues and resulting in high morbidity and mortality. Melanoma is one of the most aggressive cancer types in humans. Melanoma accounts for only about 4% of skin cancers but for as many as 74% of all skin cancer deaths. The worldwide incidence of melanoma has increased over the past few decades, with more than 132,000 people diagnosed with the disease every year (World Health Organization). In the United States, nearly 9,500 individuals will die of melanoma in 2013 (Siegel et al., CA Cancer J. Clin., 2013, 63: 11-30). If melanoma is diagnosed early, it can be cured by surgical excision and this is what occurs in about 80% of the cases. However, metastatic melanoma is refractory to current therapies and has a poor prognosis with a median survival rate of 6 months.

The prognosis of melanoma is based on histopathological criteria described in the American Joint Committee on Cancer (AJCC) melanoma staging system. These include the Breslow index, mitotic rate, ulceration status and extent of lymph node involvement (Balch et al., J. Clin. Oncol., 2009, 27: 6199-6206). Despite this staging system, the clinical behavior of melanoma is often unpredictable (Nagore et al., Melanoma Res., 2005, 15: 169-177) because melanoma is a group of diseases with various biological subtypes (Lomas et al., Front Biosci., 2008, 13: 5071-5093). In addition, patients with melanoma metastatic to the skin show variable survival: some may survive a long time, whereas some die of disseminated disease within one year of removal of skin metastases (Hofmann-Wellenhof et al., J. Cutan. Pathol., 1996, 23: 199-204).

Studies based on melanoma gene expression profiling have been performed in order to improve the prognosis of the disease and to predict the response of patients to treatment (Hoek, Pigment Cell Res., 2007, 20: 466-484). First, a comparison of gene expression profiles of normal skin, nevi and primary and metastatic melanomas has identified 2602 signature genes that could be used to distinguish two metastatic patterns, which are already emergent in large melanoma primaries (Haqq et al., Proc. Natl. Acad. Sci. USA, 2005, 102: 6092-6097). Second, cDNA expression microarray in primary melanoma has revealed a signature of 254 genes characterizing patients at risk of developing distant metastases (Winnepennincks et al., J. Natl. Cancer Inst., 2006, 98: 472-482). Third, high-throughput gene microarray in metastatic melanoma has determined a set of 80 probes (70 genes) associated with survival (Mandruzzato et al., J. Transl. Med., 2006, 4: 50). Finally, molecular profiling of lymph node metastases of stage III melanoma patients has disclosed 21 genes whose expression levels correlated with clinical outcome (John et al., Clin. Cancer, 2008, 14: 5173-5180). Thus, several new marker genes have shown promise, and large scale studies are now warranted to clinically validate them for the development of new prognostic tools, diagnostic approaches and biological-targeted therapies (Larson et al., Nat. Clin. Pract. Oncol., 2009, 6: 105-117).

Such gene discovery platforms may help to identify new molecular markers in melanoma metastases, enabling one to redefine the prognosis at the time of tumor progression, especially in thin melanomas. They may also help to establish a prognosis in patients with unknown melanoma primaries (2-6% of all melanoma cases) (Schlagenhauff et al., Cancer, 1997, 80: 60-65). The identification of such markers in high-risk melanoma patients would be important for designing and interpreting clinical trials and could be of great benefit as one might also foresee the development of useful and effective adjuvant therapies.

Thus, even though progress has been made in the field, there still remains, in the art, an ongoing need for new strategies for the treatment and/or management of metastatic melanoma, and for the development of prognostic tools.

SUMMARY OF THE INVENTION

The present Applicants have recently reported a gene profiling study in skin and in lymph nodes (which are the most frequent melanoma metastases) that shows an inverse correlation between tyrorinase-related protein 1 (TYRP1) expression level and melanoma patient overall survival (Journe et al., Br. J. Cancer, 2011, 105: 1726-1732). The Applicants' subsequent validation study using quantitative PCR only in skin metastases further supported TYRP1 as a new marker of poor clinical outcome (Journe et al., Br. J. Cancer, 2013, 108: 1641-1647). By further studying the role of TYRP1 in melanoma, the Applicants have now found that TYRP1 acts as a natural miRNA sponge and indirectly controls melanoma aggressiveness via sequestration of micro-RNAs (miRNAs), thus preventing them from exerting their anti-tumoral action. Indeed, the Applicants observed that the silencing of TYRP1 RNA transcript by RNA interference (RNAi) leads to the release of several miRNAs, which are then able to target accessible binding sites on other mRNAs whose down-regulation explains the loss of aggressiveness of melanoma in response to TYRP1 knockdown. The miRNAs that are released by silencing of TYRP1 RNA transcript were found to be miR-155, miR-133, miR-197, miR-330, and miR-16.

Accordingly, in one aspect, the present invention provides a micro-RNA inhibitor for use in the treatment of melanoma in a subject or for use in the treatment, prevention or delay of metastatic melanoma in a subject, wherein the micro-RNA inhibitor is selected from the group consisting of miR-155 inhibitors, miR-133 inhibitors, miR-197 inhibitors, miR-330 inhibitors, and miR-16 inhibitors.

In certain preferred embodiments, a micro-RNA inhibitor according to the present invention is a micro-RNA target site blocker, and is selected from the group consisting of miR-155 target site blockers, miR-133 target site blockers, miR-197 target site blockers, miR-330 target site blockers and miR-16 target site blockers.

In certain embodiments, the micro-RNA target site blocker is a miR-155 target site blocker that binds to SEQ ID NO: 8.

In certain embodiments, the miR-155 target site blocker is miR-3123, the natural target site blocker of miR-155 that functions as a bona fide miRNA.

In certain embodiments, the micro-RNA target site blocker is a miR-16 target site blocker that binds to a sequence selected from the group consisting of SEQ ID NO: 9, SEQ ID NO: 10 and SEQ ID NO: 11.

In a first related aspect, the present invention provides a pharmaceutical composition for use in the treatment of melanoma in a subject or for use in the treatment, prevention or delay of metastatic melanoma in a subject, wherein said pharmaceutical composition comprises at least one micro-RNA inhibitor and at least one pharmaceutically acceptable carrier or excipient, and wherein the micro-RNA inhibitor is an inhibitor of a micro-RNA selected from the group consisting of miR-155, miR-133, miR-197 miR-330, and miR-16.

In certain preferred embodiments, the at least one micro-RNA inhibitor present in a pharmaceutical composition according to the present invention is a micro-RNA target site blocker, and is selected from the group consisting of miR-155 target site blockers, miR-133 target site blockers, miR-197 target site blockers, miR-330 target site blockers and miR-16 target site blockers.

In certain embodiments, the micro-RNA target site blocker is a miR-155 target site blocker that binds to SEQ ID NO: 8.

In certain embodiments, the miR-155 target site blocker is miR-3123, the natural target site blocker of miR-155 that functions as a bona fide miRNA.

In certain embodiments, the micro-RNA target site blocker is a miR-16 target site blocker that binds to a sequence selected from the group consisting of SEQ ID NO: 9, SEQ ID NO: 10 and SEQ ID NO: 11.

In certain embodiments, the pharmaceutical composition comprises a combination of (i.e., at least two) micro-RNA inhibitors selected from the group consisting of miR-155 inhibitors, miR-133 inhibitors, miR-197 inhibitors, miR-330 inhibitors, and miR-16 inhibitors, and at least one pharmaceutically acceptable carrier or excipient.

In certain embodiments, the pharmaceutical composition comprises a combination (i.e., at least two) micro-RNA target site blockers selected from the group consisting of miR-155 target site blockers, miR-133 target site blockers, miR-197 target site blockers blockers, miR-330 target site blockers and miR-16 target site blockers, and at least one pharmaceutically acceptable carrier or excipient.

In another related aspect, the present invention provides a method for treating melanoma in a subject or for treating, preventing or delaying metastatic melanoma in a subject, the method comprising a step of administering to the subject at least one micro-RNA inhibitor or a pharmaceutical composition thereof, wherein the micro-RNA inhibitor is selected from the group consisting of miR-155 inhibitors, miR-133 inhibitors, miR-197 inhibitors blockers, miR-330 target site blockers, miR-16 target site blockers, and any combination thereof.

In certain preferred embodiments, the micro-RNA inhibitor administered to the patient is a micro-RNA target site blocker, and is selected from the group consisting of miR-155 target site blockers, miR-133 target site blockers, miR-197 target site blockers, miR-330 target site blockers, miR-16 target site blockers.

In certain embodiments, the micro-RNA target site blocker is a miR-155 target site blocker that binds to SEQ ID NO: 8.

In certain embodiments, the miR-155 target site blocker is miR-3123, the natural target site blocker of miR-155 that functions as a bona fide miRNA.

In certain embodiments, the micro-RNA target site blocker is a miR-16 target site blocker that binds to a sequence selected from the group consisting of SEQ ID NO: 9, SEQ ID NO: 10 and SEQ ID NO: 11.

In certain embodiments, the micro-RNA inhibitor is administered to the subject in a therapeutically effective amount.

In certain embodiments, only one micro-RNA inhibitor is administered to the subject. In other embodiments, a combination of (i.e., at least two) micro-RNA inhibitors is administered to the subject.

MiR-155, one of the miRNAs that are released by silencing of TYRP1, is known to have three binding sites (sites I, II and III) on TYRP1 mRNA 3'UTR (the three prime untranslated region of TYRP1 mRNA), two of which (sites II and III) are polymorphic sites (Li et al., PLoS Genet., 2012, 8(3): e1002578). The two SNPs, rs683 and rs910, reside within sites II and III respectively, with the derived alleles forming intact miRNA binding sites in African and Asian populations (haplotype C/A, having the "C" allele for rs683 and the "A" allele for rs910). In contrast, ⅔ of the European population carry the ancestral alleles (haplotype A/C, having the "A" allele for rs683 and the "C" allele for rs910) that alter miRNA-target interaction.

Accordingly, in certain embodiments of the present invention, the micro-RNA inhibitor used in the treatment of melanoma or in the treatment, prevention or delay of metastatic melanoma is a miR-155 target site blocker that binds to site II or to site III of TYRP1 mRNA 3'UTR, when the TYRP1 mRNA is of haplotype A/C but not when the TYRP1 mRNA is of haplotype C/A. In certain embodiments, the miR-155 target site blocker is isolated miR-3123 miR-3123 is the natural target site blocker of miR-155; it functions as a bona fide miRNA.

The present Applicants have also shown that the silencing of TYRP1 by RNA interference (RNAi) decreases the expression of the following genes: RasGRP3, MAFF, PLA2G6, RAB17, NRTN, and BAIAP2L2. These competing gene RNA transcripts were found to be sensitive to at least one of the micro-RNAs that are sequestered by TYRP1 RNA transcript (i.e., to be sensitive to miR-155, miR-133, miR-197, miR-16 and/or miR-330). The Applicants have further demonstrated that the direct silencing of RAB17 led to melanocytes morphological modifications and to a decrease in melanocytes proliferation ability and optionally migration and/or invasion ability.

Accordingly, in a second aspect, the present invention relates to an isolated RNAi agent for use in the treatment of melanoma in a subject or for use in the treatment, prevention or delay of metastatic melanoma in a subject, wherein the isolated RNAi agent inhibits the expression of at least one of human genes: RasGRP3, MAFF, PLA2G6, RAB17, NRTN, and BAIAP2L2.

Generally, an isolated RNAi agent according to the invention comprises a strand having a sequence sufficiently complementary to at least one of human RasGRP3 mRNA (or circRNA), human MAFF mRNA (or circRNA), human PLA2G6 mRNA (or circRNA), human RAB17 mRNA (or circRNA), human NRTN mRNA (or circRNA), and human BAIAP2L2 mRNA (or circRNA) to inhibit or prevent expression of the corresponding gene (i.e., RasGRP3, MAFF, PLA2G6, RAB17, NRTN, and BAIAP2L2, respectively).

In certain embodiments, the isolated RNAi agent is a micro-RNA. In other embodiments, the isolated RNAi agent is a siRNA. In yet other embodiments, the isolated RNAi agent is a shRNA. In still other embodiments, the isolated RNAi agent is a aiRNA.

In a related aspect, the present invention provides a pharmaceutical composition comprising at least one isolated RNAi agent, as defined herein, and at least one pharmaceutically acceptable carrier or excipient, for use in the treatment of melanoma in a subject or for use in the treatment, prevention or delay of metastatic melanoma in a subject.

In another aspect, the present invention provides a method for treating melanoma in a subject or for treating, preventing or delaying metastatic melanoma in a subject, the method comprising a step of silencing, by RNA interference, at least one of human gene selected from the group consisting of RasGRP3, MAFF, PLA2G6, RAB17, NRTN, and BAIAP2L2.

In certain embodiments, the step of silencing by RNA interference comprises administering to the subject a therapeutically effective amount of an isolated RNAi agent, as defined herein, or a pharmaceutical composition thereof.

The present Applicants have also shown that the presence of a low concentration of miR-155 in a biological sample obtained from a melanoma patient is indicative of a potentially aggressive melanoma (i.e., indicative of a metastatic melanoma or of a melanoma that is highly likely to rapidly become metastatic). Furthermore, the present Applicants have demonstrated that the presence of a low concentration of miR-155 in a biological sample obtained from a melanoma patient together with high levels of TYRP1 RNA transcript and MITF RNA transcript and the presence of a haplotype A/C for SNPs rs683 and rs910 of TYRP1 is indicative of a potentially aggressive melanoma (i.e., indicative of a metastatic melanoma or of a melanoma that is highly likely to rapidly become metastatic).

Accordingly, in another aspect, the present invention provides a method for predicting the therapeutic responsiveness of a melanoma patient to a therapeutic treatment targeting TYRP1 RNA transcript, the method comprising steps of: determining the level of miR-155 in a biological sample obtained from the melanoma patient, and comparing the level of miR-155 in the biological sample obtained for the melanoma patient to the level of miR-155 measured in a biological sample obtained from at least one healthy subject and/or to the level of miR-155 measured in a biological sample obtained from at least one patient diagnosed with non-metastatic melanoma. In certain embodiments, a level of miR-155 that is lower than the level of miR-155 measured in a biological sample obtained from a healthy subject or a pool of healthy subjects indicates that the melanoma patient is expected to be therapeutically responsive to a treatment targeting TYRP1 RNA transcript. In certain embodiments, a level of miR-155 that is lower than the level of miR-155 measured in a biological sample obtained from a control patient diagnosed with non-metastatic melanoma or a pool of control patients diagnosed with non-metastatic melanoma indicates that the melanoma patient is expected to be therapeutically responsive to a treatment targeting TYRP1 RNA transcript.

In certain embodiments, the level of miR-16 is determined in the biological sample obtained from the melanoma patient (instead of the level of miR-155). A level of miR-16 that is higher than the level of miR-16 measured in a biological sample obtained from a control patient diagnosed with non-metastatic melanoma or a pool of control patients diagnosed with non-metastatic melanoma indicates that the melanoma patient is expected to be therapeutically responsive to a treatment targeting TYRP1 RNA transcript. Indeed, since miR-16 is the active molecule targeting RAB17, the presence of miR-16 measured in a biological sample obtained from a patient with metastatic melanoma indicates that the melanoma patient is expected to be therapeutically responsive to a treatment targeting TYRP1 RNA transcript.

In yet other embodiments, both the level of miR-155 and the level of miR-16 are determined.

In certain embodiments, the method further comprises steps of: determining the level of TYRP1 RNA transcript (mRNA and/or circRNA) in a biological sample obtained from the melanoma patient, and comparing the level of TYRP1 RNA transcript in the biological sample obtained from the melanoma patient to the level of TYRP1 RNA transcript measured in a biological sample obtained from at least one healthy subject and/or to the level of TYRP1 RNA transcript measured in a biological sample obtained from at least one control patient diagnosed with non-metastatic melanoma. In certain embodiments, a level of TYRP1 RNA transcript (mRNA and/or circRNA) that is higher than the level of TYRP1 RNA transcript (mRNA and/or circRNA) measured in a biological sample obtained from a healthy subject or a pool of healthy subjects indicates that the melanoma patient is expected to be therapeutically responsive to a treatment targeting TYRP1 RNA transcript. In certain embodiments, a level of TYRP1 RNA transcript (mRNA and/or circRNA) that is higher than the level of TYRP1 RNA transcript (mRNA and/or circRNA) measured in a biological sample obtained from a control patient diagnosed with non-metastatic melanoma or a pool of control patients diagnosed with non-metastatic melanoma indicates that the melanoma patient is expected to be therapeutically responsive to a treatment targeting TYRP1 RNA transcript.

In certain embodiments, the method further comprises steps of: determining the level of MITF RNA transcript (mRNA and/or circRNA) in a biological sample obtained from the melanoma patient, and comparing the level of MITF RNA transcript in the biological sample obtained from the melanoma patient to the level of MITF RNA transcript measured in a biological sample obtained from at least one healthy subject and/or to the level of MITF RNA transcript measured in a biological sample obtained from at least one control patient diagnosed with non-metastatic melanoma. In certain embodiments, a level of MITF RNA transcript (mRNA and/or circRNA) that is higher than the level of MITF RNA transcript (mRNA and/or circRNA) measured in a biological sample obtained from a healthy subject or a pool of healthy subjects indicates that the melanoma patient is expected to be therapeutically responsive to a treatment targeting TYRP1 RNA transcript. In certain embodiments, a level of MITF RNA transcript (mRNA and/or circRNA) that is higher than the level of MITF mRNA measured in a biological sample obtained from a control patient diagnosed with non-metastatic melanoma or a pool of control patients diagnosed with non-metastatic melanoma indicates that the melanoma patient is expected to be therapeutically responsive to a treatment targeting TYRP1 RNA transcript.

In certain embodiments, the method further comprises steps of: determining the level of RAB17 RNA transcript (mRNA and/or circRNA) in a biological sample obtained from the melanoma patient, and comparing the level of RAB17 RNA transcript in the biological sample obtained from the melanoma patient to the level of RAB17 RNA transcript measured in a biological sample obtained from at least one healthy subject and/or to the level of RAB17 RNA transcript measured in a biological sample obtained from at least one control patient diagnosed with non-metastatic melanoma. In certain embodiments, a level of RAB17 RNA transcript (mRNA and/or circRNA) that is higher than the level of RAB17 RNA transcript (mRNA and/or circRNA) measured in a biological sample obtained from a healthy subject or a pool of healthy subjects indicates that the melanoma patient is expected to be therapeutically responsive to a treatment targeting TYRP1 RNA transcript. In certain embodiments, a level of RAB17 RNA transcript (mRNA and/or circRNA) that is higher than the level of RAB17 mRNA measured in a biological sample obtained from a control patient diagnosed with non-metastatic melanoma or a pool of control patients diagnosed with non-metastatic melanoma indicates that the melanoma patient has a poor prognostic.

In certain embodiments, the method further comprises a step of: determining the haplotype for SNPs rs683 and rs910 of TYRP1 mRNA for the melanoma patient, wherein a haplotype A/C indicates that the melanoma patient is expected to be therapeutically responsive to a treatment targeting TYRP1 mRNA.

The biological sample obtained from the melanoma patient may be from a primary tumor (e.g., cutaneous primary tumor) or from metastases (e.g., cutaneous metastases and/or lymph node metastases). The biological sample obtained from the control patient diagnosed with non-metastatic melanoma or pool of control patients diagnosed with non-metastatic melanoma may be from a primary tumor (e.g., cutaneous primary tumor). Preferably, the biological sample obtained from the healthy subject or pool of healthy subjects is a primary culture of melanocytes (e.g., from a skin sample).

In certain embodiments, the method further comprises a step of: if the melanoma patient is expected to be therapeutically responsive, administering to the melanoma patient a therapeutic treatment targeting TYRP1 RNA transcript.

In certain embodiments, the therapeutic treatment targeting TYRP1 RNA transcript comprises silencing of TYRP1 by RNA interference. For example, the therapeutic treatment targeting TYRP1 RNA transcript may comprise administration of a micro-RNA inhibitor selected from the group consisting of miR-155 inhibitors, miR-133 inhibitors, miR-197 inhibitors, miR-330 inhibitors, and miR-16 inhibitors. The micro-RNA inhibitors may be micro-RNA target site blockers. In certain embodiments, the miR-155 target site blocker is miR-3123. In certain embodiments, the micro-RNA target site blocker is a miR-16 target site blocker that binds to a sequence selected from the group consisting of SEQ ID NO: 9, SEQ ID NO: 10 and SEQ ID NO: 11.

In yet another aspect, the present invention provides a method for assessing the effectiveness of a therapeutic treatment targeting TYRP1 RNA transcript that is administered to a melanoma patient, the method comprising a step of: determining the amount of miR-155 and/or of miR-16 in a biological sample obtained from the melanoma patient after treatment, wherein an amount of miR-155 and/or of miR-16 that is higher than the amount of miR-155 and/or of miR-16 measured in a biological sample obtained from the patient before treatment indicates that the treatment targeting TYRP1 RNA transcript is effective in the patient.

In certain embodiments, the method further comprises a step of: determining the amount of TYRP1 RNA transcript (mRNA and/or circRNA) and/or of MITF RNA transcript (mRNA and/or circRNA) and/or of RAB17 RNA transcript (mRNA and/or circRNA) in a biological sample obtained from the melanoma patient after treatment, wherein an amount of TYRP1 RNA transcript (mRNA and/or circRNA) and/or of MITF RNA transcript (mRNA and/or circRNA) and/or of RAB17 RNA transcript (mRNA and/or circRNA) that is lower than the amount of TYRP1 RNA transcript (mRNA and/or circRNA) and/or of MITF RNA transcript (mRNA and/or circRNA) and/or of RAB17 RNA transcript (mRNA and/or circRNA) measured in a biological sample obtained from a biological sample obtained from the patient before treatment indicates that the treatment targeting TYRP1 RNA transcript is effective in the patient.

In certain embodiments, the therapeutic treatment targeting TYRP1 RNA transcript comprises silencing of TYRP1 by RNA interference. For example, the therapeutic treatment targeting TYRP1 RNA transcript may comprise administration of a micro-RNA inhibitor selected from the group consisting of miR-155 inhibitors, miR-133 inhibitors, miR-197 inhibitors, miR-330 inhibitors, and miR-16 inhibitors. The micro-RNA inhibitors may be micro-RNA target site blockers. In certain embodiments, the miR-155 target site blocker is miR-3123, the natural target site blocker of miR-155 that functions as a bona fide miRNA. In certain embodiments, the micro-RNA target site blocker is a miR-16 target site blocker that binds to a sequence selected from the group consisting of SEQ ID NO: 9, SEQ ID NO: 10 and SEQ ID NO: 11.

These and other objects, advantages and features of the present invention will become apparent to those of ordinary skill in the art having read the following detailed description of the preferred embodiments.

BRIEF DESCRIPTION OF THE FIGURES

FIG. 4. TYRP1 3'UTR shares miRNA with other mRNA. (A) mRNA expression levels of A2M, MAFF, NRTN, PLA2G6, Rab17 and RasGRP3 in response to TYRP1 knock-down using three different siRNA (#1-3) targeting the ORF of TYRP1 in 501Mel cells. Three days post-transfection, mRNA levels were quantified by RT-qPCR. (B) mRNA expression levels of TYRP1, Rab17, MAFF and NRTN in response to miRNA mimics transfection in 501Mel cells. Three days post-transfection, mRNA levels were quantified by RT-qPCR. (C) Luciferase assay performed 48 hours after co-transfection (miRNA mimics and 3'UTR of Rab17 fused with luciferase reporter) in 501Mel cells. (D) Rab17 protein expression levels determined by western-blot 48 hours after transfection of miRNA mimics in 501Mel cells. (E) Sponge effect of TYRP1 3'UTR. 501Mel cells were co-transfected with a miR-155 sponge (3'UTR of TYRP1 (C/A) or CTR sequence) and miRNA sensor (3'UTR Rab17 fused to luciferase reporter). Forty height hours after co-transfection, luciferase assay was performed. The one-tailed Student's t test was used; *p<0.05.

DEFINITIONS

Figure 1G:
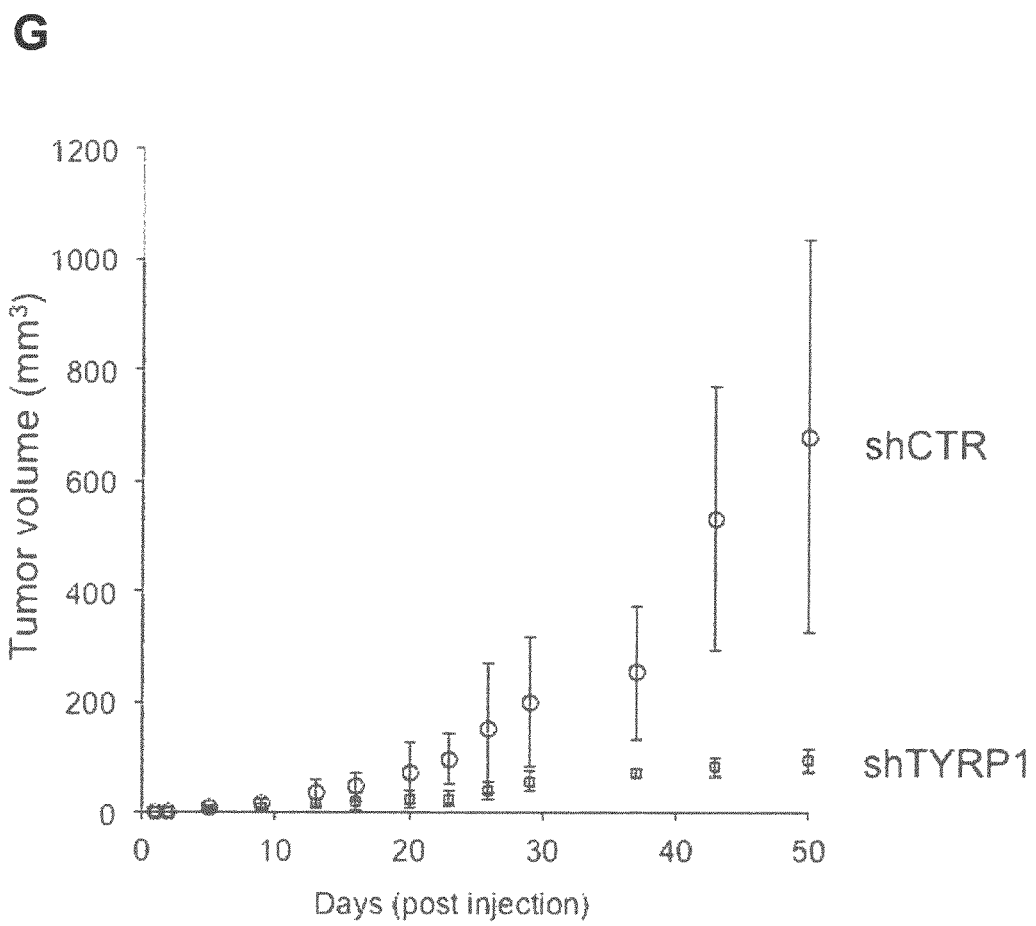
FIG. 1. Loss of 3'UTR TYRP1 decreases melanoma aggressiveness. (A) Phase-contrast images of ME1402 and 501Mel melanoma cells in mock, shSCR (shRNA control) and shTYRP1 conditions, seven days after lentiviral infection. M234 and A375P melanoma cells that do not express TYRP1 were also infected and next photographed under the same conditions. (B) Efficiency of lentiviral transduction of shRNA targeting TYRP1 mRNA was evaluated at mRNA and protein levels in ME1402 and 501Mel melanoma cell lines. Alpha-tubulin protein levels are used as loading controls. (C) Proliferation assay on ME1402 and 501Mel cells. Cells were grown in medium with 5% FBS, and counted every 2 days during 6 days (2 experiments in triplicate). Each point constituting the curves represents the mean of the replicates. (D) Proliferation index was determined in 20 melanoma cell lines. Two groups were defined in function of TYRP1 mRNA expression level (high or low). Test Mann-Whitney; **: $p<0.01$. (E) Impact of TYRP1 silencing on 501Mel cell motility. Cell migration was assayed using 24-well 8 µm transwell polycarbonate microporous filters (Corning). Starved cells were seeded in the upper chamber of the transwell and let to migrate for 24 hours at 37° C., using serum-enriched medium as chemo-attractant in the low chamber. Cells that had migrated to the lower side of the transwell membrane were fixed, stained with Crystal Violet and counted under 20× magnification. For each membrane, four fields were photographed and counted. Each histogram represents the mean value of a total of 24 fields. (F) Impact of TYRP1 silencing on SKMel28 metastatic melanoma cell invasiveness. The invasiveness of SKMel28 cells was assessed with 24-well BD Matrigel™ Invasion Chamber Inserts. Cells were placed in the upper chamber of the invasion chamber in serum-free medium, and the lower chamber was filled with medium supplemented with 10% FBS. Cells were incubated for 24 hours at 37° C. At the end of the experiment, cells that had migrated to the lower side of the filter were fixed, stained with Crystal Violet and photographed at 10× magnification. For each filter, five fields were photographed. The histogram bars represent the mean value obtained from 30 counted fields, from two independent experiments. (G) Primary tumor growth by $3 \times 10^6$ SKMel28 cells (shCTRL or shTYRP1) following subcutaneous injection into nude mice. n=5-7.

Throughout the specification, several terms are employed that are defined in the following paragraphs.

As used herein, the term "TYRP1" refers to the gene that encodes an enzyme called tyrosinase-related protein 1 or TYRP1. This enzyme is located in melanocytes and plays an important role in the melanin biosynthetic pathway. Defects in TYRP1 are the cause of different forms of albinism. More specifically, the term "TYRP1" refers to the human TYRP1 gene that is located on the short (p) arm of chromosome 9 at position 23, and more precisely from base pair 12,693,384 to base pair 12,710,284 on chromosome 9. The mRNA sequence of TYRP1 is given by GenBank Accession Numbers RefSeq(mRNA): NM_000550.1 and NM_000550.2, and the corresponding protein sequence is given by GenBank Accession Number RefSeq(protein): NP_000541.1.

As used herein, the term "gene" refers to a polynucleotide (e.g., DNA) that encodes a discrete macromolecular product, be it a RNA or a protein, and may include regulatory sequences preceding (5' non-coding sequences) and following (3' non-coding sequences) the coding sequence. As more than one polynucleotide may encode a discrete product, the term also include alleles and polymorphisms of a gene that encode the same product, or a functionally associated (including gain, loss, or modulation of function) analog thereof. The term "gene expression" refers to the process by which RNA and proteins are made from the instructions encoded in genes. Gene expression includes transcription and/or translation of nucleic acid material. The term "RNA transcript" refers to the product resulting from transcription of a DNA sequence. When the transcript is the original, unmodified product of a RNA polymerase catalyzed transcription, it is referred to as the primary transcript. An RNA transcript that has been processed (e.g., spliced, etc) will differ in sequence from the primary transcript. A processed RNA transcript that is translated into protein is often called a messenger RNA (mRNA). The term "messenger RNA or mRNA" refers to a form of RNA that serves as a template to direct protein biosynthesis. Typically, the amount of any particular type of mRNA (i.e., having the same sequence, and originating from the same gene) represents the extent to which a gene has been expressed. The term "RNA transcript" also encompasses circular RNA (circRNA). The term "circular RNA or circRNA" refers to a non-coding RNA molecule harboring exons out of order from genomic context, a phenomenon termed "exon shuffling" or "non-colinear splicing". Recent studies have suggested that circRNAs play important regulatory roles in micro-RNA activity. Thus the term "TYRP1 RNA transcript" encompasses TYRP1 mRNA and TYRP1 circRNA. The term "complementary DNA or cDNA" refers to a DNA molecule that is complementary to mRNA. The term "complementary" refers to nucleic acid sequences that base-pair according to the standard Watson-Crick complementary rules, or that are capable of hybridizing to a particular nucleic acid segment under relatively stringent conditions. Nucleic acid polymers are optionally complementary across only portions of their entire sequences.

The terms "RNA", "RNA molecule" and "ribonucleic acid molecule" are used herein interchangeably. They refer to a polymer of ribonucleotides. The terms "DNA", "DNA molecule" and "deoxyribonucleic acid molecule" are used herein interchangeably. They refer to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively.

As used herein, the term "RNA interference" (or "RNAi") has its art understood meaning and refers to a biological process in which RNA molecules silence, inhibit or down regulate gene expression by causing the destruction/degradation/cleavage of specific mRNA molecules or by blocking the translation thereof. As known in the art, RNA interference is now exploited in therapy. Indeed, RNAi can be initiated by the hand of man, for example, to silence the expression of target genes.

The terms "RNAi agent" and "interfering RNA" (or "iRNA") are used herein interchangeably. They refer to any RNA molecule that is capable of specifically inhibiting or down-regulating the expression of target gene. By "silencing, inhibiting or down-regulating expression of a target gene", it is meant that the expression of the target gene, or level of RNA molecules or equivalent RNA molecules encoding one or more proteins or protein subunits, or activity of one or more proteins or protein subunits, is reduced below that observed in the absence of the RNAi agent.

A RNAi agent may be any single-stranded RNA (e.g., mature miRNA, ssRNAi oligonucleotides, ssDNAi oligonucleotides) or double-stranded RNA (i.e., duplex RNA such as siRNA, Dicer-substrate dsRNA, shRNA, aiRNA, or pre-miRNA) that is capable of reducing or inhibiting the expression of a target gene or sequence (e.g., by mediating the degradation or inhibiting the translation of mRNAs which are complementary to the interfering RNA sequence) when the RNAi agent is in the same cell as the target gene or sequence. The term "RNAi agent" thus refers to the single-stranded RNA that is complementary to a target mRNA sequence (or circRNA sequence) or to the double-stranded RNA formed by two complementary strands or by a single, self-complementary strand. A RNAi agent may have substantial or complete identity to the target gene mRNA (or circRNA) or sequence, or may comprise a region of mismatch (i.e., a mismatch motif). As used herein, the term "mismatch motif" refers to a portion of an RNAi agent sequence that does not have 100% complementarity to its target sequence. An RNAi agent may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides. Consequently, the term "RNAi agent" refers to a RNA molecule comprising a strand having a sequence sufficiently complementary to a target mRNA (or circRNA) sequence to direct target-specific RNA interference (RNAi) thereby inhibiting or down-regulating the expression of the target gene.

An RNAi agent can comprise naturally occurring RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end of the molecule or to one or more internal nucleotides of the RNAi, including modifications that make the RNAi agent resistant to nuclease digestion.

An RNAi agent may be administered in free (naked) form or by the use of delivery systems that enhance stability and/or targeting, e.g., liposomes, or incorporated into other vehicles, such as hydrogels, cyclodextrins, biodegradable nanocapsules, bioadhesive microspheres, or proteinaceous vectors (WO 00/53722), or in combination with a cationic peptide (US 2007/275923). RNAi agents may also be administered in the form of their precursors or encoding DNAs.

In certain preferred embodiments of the present invention, an RNAi agent is a siRNA (small interfering RNA), a shRNA (short hairpin RNA), a micro-RNA (micro RNA), or an aiRNA (asymmetric interfering RNA). The development of any type of RNAi agent capable of specifically silencing, inhibiting or down-regulating the expression of a given target gene is within the capabilities of one skilled in the art. Thus, for example, siRNAs are usually designed against a region 50-100 nucleotides downstream the translation initiator codon, whereas 5'UTR (untranslated region) and 3'UTR are usually avoided. The chosen siRNA target sequence should be subjected to a BLAST search against EST database to ensure that the only desired gene is targeted. Various products are commercially available to aid in the preparation and use of siRNA. The use of RNAi agents, such as siRNAs, shRNAs, micro-RNAs or aiRNAs, to inhibit gene expression is well known in the art.

The terms "small interfering RNA" and "siRNA" are used herein interchangeably. They refer to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs).

The terms "asymmetric interfering RNA" and "aiRNA" refers to a siRNA which is characterized by the length asymmetric between the two RNA strands.

The term "short hairpin RNA" (or shRNA) refers to a sequence of RNA having one or more loop structures and a stem comprising self-complementary sense and antisense regions, wherein the antisense region comprises a sequence complementary to a region of the target mRNA. A short hairpin RNA is cleaved by the cellular machinery into siRNA. The stem can be 29, 28, 27, 26, 25, 24, 23, 22, 21, 20, 19, 18, 17, 16, 15, 14, 13, 12, 11 or 10 base pairs in length, for example between 19 and 25 base pairs, or between 19 and 21 base pairs in length. The loop can vary in length. For example, the loop may be 5, 6, 7, 8, 9, 10, 11, 12 or 13 nucleotides in length. The hairpin structure can also contain 3' or 5' overhang portions. For example, the overhang is a 3' or a 5' overhang 0, 1, 2, 3, 4 or 5 nucleotides in length.

The term "micro-RNA" (or "miRNA"), as used herein, has its art understood meaning. Micro-RNAs are a major group of noncoding RNAs that are known to regulate almost a third of all the coding genes. They are small (~20-25 nucleotides long) endogenously formed repressors of gene expression. miRNAs usually bind to the 3' untranslated region (3'UTR) of the target RNA transcripts (mRNAs or circRNAs) and are capable of inducing posttranscriptional gene regulation by blocking translation or by degrading the target RNAs, or by doing both. miRNAs can also be chemically synthesized. In contrast to siRNA, which has perfect complementarity to the target RNA transcripts, miRNA binds imperfectly to the target RNA transcripts.

The term "micro-RNA inhibitor" refers to a molecule that prevents the binding between the micro-RNA and a RNA transcript target site. In many preferred embodiments of the present invention, a micro-RNA inhibitor is a micro-RNA target site blocker. The term "micro-RNA target site blocker" refers to an antisense oligonucleotide that binds to the micro-RNA target site of a RNA transcript (mRNA or circRNA) thereby preventing microRNAs from gaining access to that site. Micro-RNA target site blockers allow researchers to study the effects of a micro-RNA on a single target. In contrast, the phenotype observed with inhibiting a micro-RNA reflects the combined effects of that micro-RNA on all its targets. Micro-RNA target site blockers may also be termed MRE inhibitors. The term "micro-RNA recognition element or MRE" refers to the cis-sequence element present on the RNA transcript (mRNA or circRNA) that is recognized by miRNA, mediating their binding. The term "MRE inhibitor" refers to a short modified RNA molecule, that is resistant to RNAse H and that is capable of preventing binding of miRNA to its target by interacting directly to the MRE with high affinity.

The term "isolated", when used herein in reference to a RNA molecule or RNAi agent, means a RNA molecule or RNAi agent, which by virtue of its origin or manipulation is separated from at least some of the components with which it is naturally associated or with which it is associated when initially obtained. By "isolated", it is alternatively or additionally meant that the RNA molecule or RNAi agent of interest is produced or synthesized by the hand of man, and substantially free of culture medium when produced by recombinant technique, or substantially free of chemical precursors or other chemicals when chemically synthesized.

As used herein, the term "subject" refers to a mammal that can suffer from melanoma, but may or may not have the pathology. In many embodiments of the present invention, the subject is a human being. In such embodiments, the subject is often referred to as an "individual" or a "patient". The terms "subject", "individual" and "patient" do not denote a particular age, and thus encompass newborns, children, teenagers, and adults.

The term "melanoma patient", as used herein, refers to a patient who has been diagnosed with melanoma. The diagnostic may have been performed using any method known in the art. The present document is mainly concerned about melanoma. However, it will be obvious to one skilled in the art that the methods and therapeutic agents of the present invention also find application in the management of other types of cancers including, but not limited to, breast cancer, glioblastoma, etc.

The term "treatment" is used herein to characterize a method or process that is aimed at (1) delaying or preventing the onset of a disease or condition (here melanoma or metastatic melanoma); (2) slowing down or stopping the progression, aggravation, or deterioration of the symptoms of the disease or condition; (3) bringing about amelioration of the symptoms of the disease or condition; or (4) curing the disease or condition. A treatment may be administered prior to the onset of the disease or condition, for a prophylactic or preventive action. Alternatively or additionally, a treatment may be administered after initiation of the disease or condition, for a therapeutic action.

A method for predicting the therapeutic responsiveness of a melanoma patient to a therapeutic treatment targeting TYRP1 RNA transcript is described herein. The term "therapeutically responsive", when used herein to qualify a melanoma patient, refers to a patient suffering from melanoma or metastatic melanoma who will enjoy at least one of the following clinical benefits as a result of a therapeutic treatment targeting TYRP1 RNA transcript: amelioration of the disease, reduction in the occurrence of symptoms associated with the disease, partial remission of the disease, full remission of the disease, or increased time to progression (e.g., increased time to progression to metastatic melanoma). The therapeutic response can be full or partial response, and the method of the invention is used to determine the probability of a therapeutic response, regardless of whether it is a full or partial response.

As used herein, the term "time to progression" refers to the period, length or duration of time after a disease is diagnosed (or treated) until the disease begins to worsen (such as until a tumor begins or continues to grow or starts to metastasize). It is the period of time during which the level of a disease is maintained without further progression of the disease, and the period of time ends when the disease begins to progress again. Progression of a disease is determined by "staging" a subject suffering from melanoma prior to or at initiation of therapy. For example, the size, location and number of tumors of a subject are determined prior to or at initiation of therapy. The subject is then treated, and the size and number of tumors are monitored periodically. At some later point in time, the size and/or number of tumors may increase, thus marking progression of the disease and the end of the "time to progression". The period of time during which the disease did not progress or during which the level or severity of the disease did not worsen is the "time to progression".

The term "biological sample" is used herein in its broadest sense. A biological sample is generally obtained from a subject. A sample may be of any biological tissue or fluid with which mR-155 and/or TYRP1 RNA transcript and/or MITF RNA transcript may be assayed. Frequently, a sample will be a "clinical sample", i.e., a sample derived from a melanoma patient. Such samples include, but are not limited to, bodily fluids which may or may not contain cells, e.g., blood (e.g., whole blood, serum or plasma), urine, saliva, tissue or fine needle biopsy samples (e.g., of skin, and in particular of skin melanoma tumors), and archival samples with known diagnosis, treatment and/or outcome history. Biological samples may also include sections of tissues such as frozen sections taken for histological purposes. The term "biological sample" also encompasses any material derived by processing a biological sample. Derived materials include, but are not limited to, cells (or their progeny)

isolated from the sample, proteins or nucleic acid molecules extracted from the sample. Processing of a biological sample may involve one or more of: filtration, distillation, extraction, concentration, inactivation of interfering components, addition of reagents, and the like. In preferred embodiments of the invention, the biological sample is (or is derived from) tumor samples (primary, lymph nodes, metastases, short term culture) obtained from a subject.

The biological sample to be tested is obtained from a melanoma patient and the results of the test are compared to those obtained for biological sample obtained from a healthy subject. The terms "normal" and "healthy" are used herein interchangeably. They refer to an individual or group of individuals who do not suffer from melanoma or any other skin disease or disorder. The terms "normal" and "healthy" are also used herein to qualify a biological sample obtained from a healthy individual.

In the context of the present invention, the term "control", when used herein to characterize a subject, refers to a subject who is healthy or to a patient who has been diagnosed with non-metastatic melanoma or yet to a patient who has been diagnosed with metastatic melanoma. The term "control sample" refers to one, or more than one, sample that has been obtained from a control subject. It is known in the art that control samples are generally obtained from a cohort of healthy subjects and/or control patients.

A "pharmaceutical composition" is defined herein as comprising a therapeutically effective amount of at least one therapeutic agent (e.g., a miRNA inhibitor or RNAi agent), and at least one pharmaceutically acceptable carrier or excipient.

The term "pharmaceutically acceptable carrier or excipient" refers to a carrier medium which does not interfere with the effectiveness of the biological activity of the active ingredient(s) and which is not excessively toxic to the host at the concentration at which it is administered. The term includes solvents, dispersion, media, coatings, antibacterial and antifungal agents, isotonic agents, and adsorption delaying agents, and the like. The use of such media and agents for pharmaceutically active substances is well known in the art (see for example "Remington's Pharmaceutical Sciences", E. W. Martin, 18$^{th}$ Ed., 1990, Mack Publishing Co.: Easton, Pa., which is incorporated herein by reference in its entirety).

As used herein, the term "therapeutically effective amount" refers to any amount of a therapeutic agent or composition thereof that is sufficient to fulfil its intended purpose(s), e.g., a desired biological or medicinal response in a cell, tissue, system or subject. For example, in certain embodiments of the present invention, the purpose(s) may be: to treat melanoma or to treat, prevent or delay metastatic melanoma.

DETAILED DESCRIPTION OF THE INVENTION

The present invention relates to methods and reagents for the treatment of melanoma and/or of metastatic melanoma that directly or indirectly target or bind to TYRP1 RNA transcript (mRNA or circRNA). The invention also relates to methods for predicting if a melanoma patient will be therapeutically responsive to such methods of treatment and reagents, and to methods for assessing the effectiveness of such methods of treatment and reagents. Finally, the invention provides methods and reagents for the treatment of melanoma and/or metastatic melanoma via silencing of human genes RasGRP3, MAFF, PLA2G6, RAB17, NRTN, and BAIAP2L2.

I—Treatment of Melanoma and Metastatic Melanoma

As used herein, the term "therapeutic treatment targeting TYRP1 RNA transcript", refers to a treatment that directly or indirectly affects TYRP1 mRNA or circRNA integrity or functionality (e.g., that cleaves or destroys TYRP1 mRNA, that blocks TYRP1 mRNA transcription, that prevents normal interactions of TYRP1 mRNA with micro-RNAs, that cleaves or destroys TYRP1 circRNA, that prevents normal interactions of TYRP1 circRNA with micro-RNAs and/or that allows recruitment of RNA binding proteins that possess anti-melanoma properties).

A. Direct Silencing of TYRP1 by RNA Inference

In certain embodiments, a therapeutic method targeting TYRP1 RNA transcript according to the present invention includes direct silencing of TYRP1 by RNA interference.

Based on the sequence of human TYRP1 mRNA or circRNA or RNA splices, one skilled in the art knows how to develop RNAi agents that are capable of specifically silencing, inhibiting or down-regulating the expression of TYRP1.

B. Micro-RNA Inhibitors

In other embodiments, a therapeutic method targeting TYRP1 RNA transcript according to the present invention includes the use of at least one inhibitor of a micro-RNA that has been identified by the present Applicants as being sequestrated by TYRP1 RNA, acting as a natural micro-RNA sponge. Thus, the present invention provides a micro-RNA inhibitor for use in the treatment of melanoma or for use in the treatment, prevention or delay of metastatic melanoma, wherein the micro-RNA inhibitor is selected from the group consisting of miR-155 inhibitors, miR-133 inhibitors, miR-197 inhibitors, miR-330 inhibitors and miR-16 inhibitors.

As used herein the term "miR-155" refers to a micro-RNA that in humans is encoded by the MIR155 host gene or MIR155HG, which is located on the long (q) arm of chromosome 21 at location 21.3. The sequence of the precursor of miR-155 is given by GenBank Accession Number RefSeq(mRNA): NR_030784.1.

As used herein the term "miR-133" refers to a micro-RNA that in humans is encoded by one of the three genes: miR-133a-1, miR-133a-2 and miR-133b found on chromosomes 18, 20 and 6 respectively. The mature sequence of has-miR-133a-5p is given by Accession Number: MIMAT0026478; the mature sequence of has-miR-133a-3p is given by Accession Number: MIMAT0000427; the mature sequence of has-miR-133b is given by Accession Number: MIMAT0000770.

As used herein the term "miR-197" refers to a micro-RNA that in humans is encoded by the MIR197 gene, which is located on the short (p) arm of chromosome 1 at location 13.3. The sequence of the precursor of miR-197 is given by GenBank Accession Number RefSeq(mRNA): NR_029583.1. The mature sequence of has-mir-197-5p is given by Accession Number: MIMAT0022691, and the mature sequence of has-miR-197-3p is given by Accession Number: MIMAT0000227.

As used herein the term "miR-330" refers to a micro-RNA that in humans is encoded by the MIR1330, which is located on the long (q) arm of chromosome 19 at location 13.32. The mature sequence of has-miR-330-5p is given by Accession Number: MIMAT0004693 and the mature sequence of has-miR-330-3p is given by Accession Number: MIMAT0000751.

As used herein the term "miR-16" refers to a micro-RNA that in humans is encoded by the MIR16 host gene, which is located on the long (q) arm of chromosome 13 at location 14.2. The sequence of the precursor of miR-16 is given by GenBank Accession Number RefSeq(mRNA): MIMAT000069.

As indicated above, a micro-RNA inhibitor according to the invention is any molecule that is capable of preventing the binding between the micro-RNA to its binding site on TYRP1 RNA transcript (mRNA or circRNA).

Thus, in certain embodiments, miR-155, miR-133, miR-197, miR-330, and miR-16 may be inhibited by administering inhibitory RNA molecules each having at least partial sequence identity to a binding site of miR-155, miR-133, miR-197, miR-330, and miR-16 on TYRP1 RNA transcript. The inhibitory RNA molecules may be double-stranded, small interfering RNA (siRNA) or short hairpin RNA (shRNA) molecules. The double-stranded regions of the inhibitory RNA molecule may comprise a sequence that is at least partially identical, e.g., about 75%, 80%, 85%, 90%, 95%, 96%, 97%, 98%, or 99% identical, to at least one of the mature miR-155, miR-133, miR-197, miR-330, and miR-16 sequences. In some embodiments, the double-stranded regions of the inhibitory RNA comprise a sequence that is at least substantially identical to at least one of the mature miR-155, miR-133, miR-197, miR-330, and miR-16 sequences. The term "substantially identical" refers to a sequence that is at least about 95%, 96%, 97%, 98%, or 99% identical to a target polynucleotide sequence. In particular, the differences in homology take into account RNA editing. RNA editing is a molecular process through which some cells can make discrete changes to specific nucleotide sequences within a RNA molecule after it has been generated by RNA polymerase. Editing events may include the insertion, deletion, and base substitution of nucleotides within the edited RNA molecule. In other embodiments, the double-stranded regions of the combination of inhibitory RNA molecules may contain 100% identity to at least one of the miR-155, miR-133, miR-197, miR-330, and miR-16 sequences.

In certain embodiments, miR-155, miR-133, miR-197, miR-330, or miR-16 may be inhibited by administration of at least one micro-RNA target site blocker, i.e., an antisense oligonucleotide that binds to the micro-RNA target site of TYRP1 RNA transcript (mRNA or circRNA) thereby preventing miR-155, miR-133, miR-197, miR-330, or miR-16 from gaining access to this site. Knowing the sequences of these micro-RNAs and the sequence of TYRP1 RNA transcript (in particular the sequence of the 3'UTR region of TYRP1 mRNA—see below), one skilled in the art is able to determine the binding site(s) for each of the micro-RNAs.

In certain embodiments, only one micro-RNA inhibitor is administered to a melanoma patient.

In other embodiments, a combination (i.e., a least two) micro-RNA inhibitors is administered to the melanoma patient. For example, when two different micro-RNA inhibitors are used, the first inhibitor may be a miR-155 inhibitor and the second inhibitor may be a miR-133 inhibitor; or the first inhibitor may be a miR-155 target site blocker that binds to a first binding site of miR-155 on TYRP1 mRNA and the second inhibitor may be a miR-155 target site blocker that binds to a second binding site of miR-155 on TYRP1 mRNA. Alternatively, a first inhibitor may be a miR-16 target site blocker that binds to a first binding site of miR-16 on TYRP1 mRNA, a second inhibitor may be a miR-16 target site blocker that binds to a second binding site of miR-16 on TYRP1 mRNA, and a third inhibitor may be a miR-16 target site blocker that binds to a third binding site of miR-16 on TYRP1 mRNA (see below).

C. Personalized miR-155 Approach

In certain particular embodiments, a therapeutic method targeting TYRP1 RNA transcript (mRNA or circRNA) according to the present invention includes the use of at least one miR-155 target site blocker. As indicated above, miR-155, is known to have three binding sites (sites I, II and III) on TYRP1 mRNA 3'UTR (the three prime untranslated region of TYRP1 mRNA). The sequence of TYRP1 mRNA 3'UTR is set forth in SEQ ID NO: 1 below, wherein the three sites I, II and III are underlined and in bold.

```
SEQ ID NO: 1:
CAAAUGCCCUACUCUCUUAUGCAUUAGUAUCACAAAACCACCUGGUUG

AAUAUAAUAGAUUGAGUUAUUAACUGUAUUUUCUUUCACUUUAUUACC

UUCUUUCUAAUACAAGCAUAUGUUAGCAUUAAAGUUCUAGGCAUACUU

UUCAAAGCUGGGAAGACCCUUUCAGAAUCUUUUCAAUGGGUUUUAAUU

UUCAGUUCUAUUUAAAAUGGUGAAUGACACUAAACUCCAUGAUAUUUA

AGGAUAGUGUGAAGAUCUUUGGCAUGAUUUAAAGGUUGAGUAUGUGAA

GAUAUAAGUAAGUGAACUACCAUGCUUUGUUUACGUGUAAAGGAAAAU

AAUGUUUGAUAGUAAAAUGUCCACUUAAAAUACAUGAAUGGGCAUUUCU

AAAAUGUUAAAACAUAAACACAUUUCCAUUCAUGGAUAUUUGUCAACA

GAUUUAAAGAAAACCACAGUUAUUAAUUAAAGAAAAUUAAUUAUGUGU

AGUUAUAAACCAAUGAAAUUUUGAUUAACCUUUUCAAAUUAAUGUUCC

AGUUUGAAGACCAAUCAAAUAUAUUAUUUAGUCAACAUAUACUAUUUA

GUCUCAGGUUCAAGGCUACAACAAAAAUCACCAUCUUUGUCAAACUUU

GGAGAGGGAAAAUCUUCACUUUCUUAAGCAACAAUGGAUAUUGCCUGU

GUUUGCCACUGUGUUUCCCUGCCUCUCAAUUCGCUGAAAAAGGAACUA

CCUAUCCUUACAUUUCACCUACUAAUGUCUCUUCUAACAUCUUAGAGG

UCCAUGGAGAAGGCAUAUGGAGAACAUGUUUUAUACUGCUCUAUAAAU

AGUAUUCCAAUCACUGUGCUUAAUUUAAAUAGCAUUAUCUUAUCAUUU

AUCAGCCUUUUAUGUAUUUUCCAAGUAAAAUAUUAACAUAUUAUUUCA

UUGGUCUUCUUUUUUAUCUGGUUCUAUAUGAAUGCUAUUUUUUCCCUU

CUCUUCUAACAUGAAAUAUAUUUUCUCUUUUUGAUCUUGUGCUAUGAA

ACAAUCUUCCAAAGAACUGUAUAAGGUGGUCAUAAGUGAAUAUUUUAA

UUAAAAUUGGUAAAAAUAAAUAAUAACA
```

Site II contains SNP re683 and site III contains SNP rs910. In haplotype C/A (present in African and Asian populations), site II has the sequence set forth in SEQ ID NO: 2 (UUAGCAUUAA) and site III has the sequence set forth in SEQ ID NO: 3 (UAGCAUUA). In haplotype A/C (present in ⅔ of the European population), site II has the sequence set forth in SEQ ID NO: 4 (UUAGAAUUAA) and site III has the sequence set forth in SEQ ID NO: 5 (UAGCAUUC).

Thus, depending on the melanoma patient's TYRP1 mRNA haplotype, inhibition of miR-155 may be performed by administering a miR-155 target site blocker that binds to site II of SEQ ID NO: 2 or site III of SEQ ID NO: 3 in case of a C/A haplotype, or by administering a miR-155 target site blocker that binds to site II of SEQ ID NO: 3 or site III of SEQ ID NO: 5 in case of a A/C haplotype.

Using the known sequences of TYRP1 mRNA 3'UTR (or TYRP1 circRNA) and of site II and site III, one skilled in the art knows how to design and develop miR-155 target site blockers for each haplotype.

For example, in embodiments where the haplotype is A/C, the miR-155 target site blocker may be miR-3123.

As used herein the term "miR-3123" refers to a micro-RNA that in humans is encoded by the MIR3123 gene (the mRNA sequence of which is given by GenBank Accession Number RefSeq(mRNA): NR_036069.1. The mature sequence of has-mir-3123 is given by Accession Number: MIMAT0014985.

Consequently, in certain embodiments of the present invention, the micro-RNA inhibitor used in the treatment of melanoma or in the treatment, prevention or delay of metastatic melanoma is a miR-155 inhibitor that binds to site II or to site III of TYRP1 mRNA 3'UTR, when the TYRP1 mRNA is of haplotype A/C but not when the TYRP1 mRNA is of haplotype C/A. In certain preferred embodiments, the micro-RNA inhibitor is isolated miR-3123.

In certain embodiments, only one miR-155 target site blocker is administered to a melanoma patient. In other embodiments, two miR-155 target site blockers are administered to the melanoma patient (for example one target site blocker of each of sites II and III).

Each of sites I, II and III is the minimal binding site of miR-155 on TYRP1 mRNA 3'UTR. Each of these sites is included in a larger binding region of SEQ ID NO: 6 (GCCCUACUCUCUUAUGCAUUAGUAUC), SEQ ID NO: 7 (UACCUUCUUUCUAAUACAAGCAUAU-GUUAGCAUUAAA) and SEQ ID NO: 8 (UAUUCCAAU-CACUGUGCUUAAUUUAAAUAGCAUUAU), respectively, which are underlined in SEQ ID NO: 1 above.

The present Applicants have shown that a miR-155 target site blocker that binds to site III or more generally to the corresponding binding region of SEQ ID NO: 8 releases not only miR-155 but also miR-16.

D. miR-16 Target Site Blockers

In certain particular embodiments, a therapeutic method targeting TYRP1 RNA transcript (mRNA or circRNA) according to the present invention includes the use of at least one miR-16 target site blocker. The present inventors have found that miR-16 has three binding sites (sites I', II' and III') on TYRP1 mRNA 3'UTR (the three prime untranslated region of TYRP1 mRNA). The sequence of TYRP1 mRNA 3'UTR is set forth in SEQ ID NO: 1 below, wherein the three sites I', II' and III' are underlined.

```
SEQ ID NO: 1:
CAAAUGCCCUACUCUCUUAUGCAUUAGUAUCACAAAACCACCUGGUU

GAAUAUAAUAGAUUGAGUUAUUAACUGUAUUUUCUUUCACUUUAUUA

CCUUCUUUCUAAUACAAGCAUAUGUUAGCAUUAAAGUUCUAGGCAUA

CUUUUCAAAGCUGGGAAGACCCUUUCAGAAUCUUUUCAAUGGGUUUU

AAUUUUCAGUUCUAUUUAAAAUGGUGAAUGACACUAAACUCCAUGAU

AUUUAAGGAUAGUGUGAAGAUCUUUGGCAUGAUUUAAAGGUUGAGUA

UGUGAAGAUAUAAGUAAGUGAACUACCAUGCUUUGUUUACGUGUAAA

GGAAAAUAAUGUUUGAUAGUAAAUGUCCACUUAAAAUACAUGAAUGG

GCAUUUCUAAAAUGUUAAAACAUAAACACAUUUCCAUUCAUGGAUAU

UUGUCAACAGAUUUAAAGAAAACCACAGUUAUUAAUUAAAGAAAAUU
```
-continued
```
AAUUAUGUGUAGUUAUAAACCAAUGAAAUUUUGAUUAACCUUUUCAA

AUUAAUGUUCCAGUUUGAAGACCAAUCAAAUAUAUUAUUUAGUCAAC

AUAUACUAUUUAGUCUCAGGUUCAAGGCUACAACAAAAAUCACCAUC

UUUGUCAAACUUUGGAGAGGGAAAAUCUUCACUUUCUUAAGCAACAA

UGGAUAUUGCCUGUGUUUGCCACUGUGUUUCCCUGCCUCUCAAUUCG

CUGAAAAAGGAACUACCUAUCCUUACAUUUCACCUACUAAUGUCUCU

UCUAACAUCUUAGAGGUCCAUGGAGAAGGCAUAUGGAGAACAUGUUU

UAUACUGCUCUAUAAAUAGUAUUCCAAUCACUGUGCUUAAUUUAAAU

AGCAUUAUCUUAUCAUUUAUCAGCCUUUUAUGUAUUUUCCAAGUAAA

AUAUUAACAUAUUAUUUCAUUGGUCUUCUUUUUUAUCUGGUUCUAUA

UGAAUGCUAUUUUUUCCCUUCUCUUCUAACAUGAAAUAUAUUUUCUC

UUUUUGAUCUUGUGCUAUGAAACAAUCUUCCAAAGAACUGUAUAAGG

UGGUCAUAAGUGAAUAUUUUAAUUAAAAUUGGUAAAAAUAAAUAAUA

ACA
```

Thus, the miR-16 target site blocker may bind to site I' (of SEQ ID NO: 9: AGAAAAUUAAUUAUGU-GUAGUUAU), or to site II' (of SEQ ID NO: 10: UGCCU-GUGUUUGCCACUGUGUUUCCCUGCC) or to site III' (of SEQ ID NO: 11: UCCAAUCACUGUGCUU).

In certain embodiments, only one miR-16 target site blocker is administered to a melanoma patient. In other embodiments, two miR-16 target site blockers are administered to the melanoma patient (for example one target site blocker of each of sites II' and III'). In yet other embodiments, three miR-16 target site blockers are administered to the melanoma patient (for example one target site blocker of each of sites I', II' and III').

In still other embodiments, a melanoma patient is administered a combination of miR-155 target site blockers and miR-16 target site blockers.

E. Silencing of Competing Genes by Direct RNA Interference

The invention also relates to an isolated RNAi agent for use in the treatment of melanoma or for use in the treatment, prevention or delay of metastatic melanoma, wherein the isolated RNAi agent inhibits the expression of at least one of human genes RasGRP3, MAFF, PLA2G6, RAB17, NRTN, and BAIAP2L2. Generally, an isolated RNAi agent according to the invention comprises a strand having a sequence sufficiently complementary to at least one of human RasGRP3 RNA transcript (mRNA or circRNA), human MAFF RNA transcript (mRNA or circRNA), human PLA2G6 RNA transcript (mRNA or circRNA), human RAB17 RNA transcript (mRNA or circRNA), human NRTN RNA transcript (mRNA or circRNA), and human BAIAP2L2 RNA transcript (mRNA or circRNA) to inhibit or prevent expression of the corresponding gene (i.e., RasGRP3, MAFF, PLA2G6, RAB17, NRTN, and BAIAP2L2, respectively).

As used herein, the term "human RasGRP3" refers to the human gene that encodes the Ras guanyl-releasing protein 3. The RasGRP3 gene is located on the short arm (p) of chromosome 2. The mRNA sequence of RasGRP3 variant 1 is given by GenBank Accession Number RefSeq(mRNA): NM_001139488.1, the mRNA sequence of RasGRP3 variant 2 is given by GenBank Accession Number RefSeq (mRNA): NM_001128602.1, and the mRNA sequence of RasGRP3 variant 3 is given by GenBank Accession Number RefSeq(mRNA): NM_015376.2.

As used herein, the term "human MAFF" refers to the human gene that encodes the transcription factor, v-maf avian musculoaponeurotic fibrosarcoma oncogene homolog F or MafF. The MAFF gene is located on the large arm (q) of chromosome 22 at location 13.1. The mRNA sequence of MAFF variant 1 is given by GenBank Accession Number RefSeq(mRNA): NM_012323.3, the mRNA sequence of MAFF variant 3 is given by GenBank Accession Number RefSeq(mRNA): NM_001161572.1, the mRNA sequence of MAFF variant 4 is given by GenBank Accession Number RefSeq(mRNA): NM_001161573.1, and the mRNA sequence of MAFF variant 5 is given by GenBank Accession Number RefSeq(mRNA): NM_001161574.1.

As used herein, the term "human PLA2G6" refers to the human gene that encodes an enzyme called calcium-independent phospholipase A2. The PLA2G6 gene is located on the long (q) arm of chromosome 22 at location 13.1. The mRNA sequence of PLA2G6 variant 1 is given by GenBank Accession Number RefSeq(mRNA): NM_003560.2, the mRNA sequence of PLA2G6 variant 2 is given by GenBank Accession Number RefSeq(mRNA): NM_001004426.1, and the mRNA sequence of PLA2G6 variant 3 is given by GenBank Accession Number RefSeq(mRNA): NM_001199562.1.

As used herein, the term "human RAB17" refers to the human gene that encodes the Ras-related protein Rab-17. The RAB17 gene is located on the long (q) arm of chromosome 2 at location 37.3. The mRNA sequence of RAB17 variant 1 is given by GenBank Accession Number RefSeq (mRNA): NM_022449.3 and the mRNA sequence of RAB17 variant 2 is given by GenBank Accession Number RefSeq(mRNA): NR_033308.1.

As used herein, the term "human NRTN" refers to the human gene that encodes the protein called Neurturin, a member of the TGF-beta subfamily. The NRTN gene is located on the short (p) arm of chromosome 19 at location 13.3. The mRNA sequence of NRTN is given by GenBank Accession Number RefSeq(mRNA): NM_004558.3.

As used herein, the term "human BAIAP2L2" refers to the human gene that encodes the PaII-associated protein 2-like 2. The BAIAP2L2 gene is located on the long (q) arm of chromosome 22 at position 13.1. The mRNA sequence of BAIAP2L2 is given by GenBank Accession Number RefSeq (mRNA): NM_025045.4.

As indicated above, using the known mRNA sequences of these human genes, one skilled in the art knows how to design and develop RNAi agents that are capable of specifically inhibiting or down-regulating the expression of the target genes. It will be obvious to one skilled in the art that predicted sequences of human RasGRP3, MAFF, PLA2G6, RAB17, NRTN, and BAIAP2L2 RNA and newly discovered sequences of human RasGRP3, MAFF, PLA2G6, RAB17, NRTN, and BAIAP2L2 RNA as well as any known variants can also be utilized in the practice of the present invention to design and develop RNAi agents that are capable of specifically inhibiting or down-regulating the expression of these genes.

In certain embodiments, only one RNAi agent is administered to a melanoma patient (for example one RNAi agent that inhibits the expression of human gene RAB17). In other embodiments, a combination of (i.e., at least two) RNAi agents is administered to a melanoma patient (for example, one RNA agent that inhibits the expression of human gene RAB17 and one RNA agent that inhibits at least one of human genes: TYRP1, RasGRP3, MAFF, PLA2G6, NRTN, and BAIAP2L2).

E. Administration of RNAi Agents and Micro-RNA Inhibitors

An inventive RNAi agent or micro-RNA inhibitor, (optionally after formulation with one or more appropriate pharmaceutically acceptable carriers or excipients), in a desired dosage can be administered to a melanoma patient by any suitable route. Various delivery systems are known and can be used to administer RNAi molecules of the present invention, including tablets, capsules, injectable solutions, encapsulation in liposomes, microparticles, microcapsules, etc. Methods of administration include, but are not limited to, dermal, intradermal, intramuscular, intraperitoneal, intralesional, intravenous, subcutaneous, intranasal, pulmonary, epidural, ocular, and oral routes. An inventive RNAi agent or micro-RNA inhibitor or composition thereof may be administered by any convenient or other appropriate route, for example, by infusion or bolus injection, by absorption through epithelial or mucocutaneous linings (e.g., oral, mucosa, rectal and intestinal mucosa, etc). Administration can be systemic or local.

In certain embodiments, a RNAi agent or micro-RNA inhibitor according to the present invention is administered to a melanoma patient in combination with an additional therapeutic agent (e.g., a therapeutic agent chosen from chemotherapeutics and immunotherapeutics). In such embodiments, the RNAi agent or micro-RNA inhibitor and the therapeutic agent may be administered by the same route (e.g., intravenously) or by different routes (e.g., intravenously and orally).

In certain embodiments, a RNAi agent or micro-RNA inhibitor according to the present invention is administered in combination with a therapeutic procedure (e.g., surgical excision and/or radiation therapy). In such embodiments, the RNAi agent or micro-RNA inhibitor and the therapeutic procedure may be administered to the melanoma patient prior to the therapeutic procedure, following the therapeutic procedure or concomitantly with the therapeutic procedure.

Administration of a RNAi agent or micro-RNA inhibitor of the present invention will be in a dosage such that the amount delivered is effective for the intended purpose. The route of administration, formulation and dosage administered will depend upon the therapeutic effect desired, the severity/stage of the melanoma to be treated, the presence of any metastasis, the presence of any infection, the age, sex, weight, and general health condition of the patient as well as upon the potency, bioavailability, and in vivo half-life of the RNAi agent or micro-RNA inhibitor used, the use (or not) of concomitant therapies, and other clinical factors. These factors are readily determinable by the attending physician in the course of the therapy. Alternatively or additionally, the dosage to be administered can be determined from studies using animal models (e.g., chimpanzee or mice). Adjusting the dose to achieve maximal efficacy based on these or other methods are well known in the art and are within the capabilities of trained physicians.

A treatment according to the present invention may consist of a single dose or multiple doses. Thus, administration of a RNAi agent or micro-RNA inhibitor, or pharmaceutical composition thereof, may be constant for a certain period of time or periodic and at specific intervals, e.g., hourly, daily, weekly (or at some other multiple day interval), monthly, yearly (e.g., in a time release form). Alternatively, the delivery may occur at multiple times during a given time period, e.g., two or more times per week; two or more times per month, and the like. The delivery may be continuous delivery for a period of time, e.g., intravenous delivery.

As already mentioned above, the present document mainly concerns melanoma. However, it will be obvious to one skilled in the art that the RNAi agents and micro-RNA inhibitors according to the present invention may be used in the treatment of any other type of cancers exhibiting TYRP1 overexpression. Examples of such cancers include, but are not limited to breast cancer, glioblastoma, etc.

II—Pharmaceutical Compositions

As mentioned above, the RNAi agents and micro-RNA inhibitors of the present invention may be administered per se or as a pharmaceutical composition. Accordingly, the present invention provides pharmaceutical compositions comprising an effective amount of at least one RNAi agent or at least one micro-RNA inhibitor (as defined herein) and at least one pharmaceutically acceptable carrier or excipient. In some embodiments, the composition further comprises one or more additional biologically active agents.

The RNAi agents or micro-RNA inhibitors and pharmaceutical compositions thereof may be administered in any amount and using any route of administration effective for achieving the desired prophylactic and/or therapeutic effect. The optimal pharmaceutical formulation can be varied depending upon the route of administration and desired dosage. Such formulations may influence the physical state, stability, rate of in vivo release, and rate of in vivo clearance of the administered active ingredient.

Prior to formulation, the RNAi agents or micro-RNA inhibitors may be inserted into viral or nonviral delivery vectors (Khatri et al., Crit. Rev. Ther. Drug Carrier Syst., 2012, 29: 487-527).

The pharmaceutical compositions of the present invention may be formulated in dosage unit form for ease of administration and uniformity of dosage. The expression "unit dosage form", as used herein, refers to a physically discrete unit of an RNAi agent or micro-RNA inhibitor for the patient to be treated. It will be understood, however, that the total daily dosage of the compositions will be decided by the attending physician within the scope of sound medical judgement.

A. Formulation

Injectable preparations, for example, sterile injectable aqueous or oleaginous suspensions may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered, for example, by intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient, it is often desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly(orthoesters) and poly (anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the RNAi agent or micro-RNA inhibitor, the liquid dosage form may contain inert diluents commonly used in the art such as, for example, water or other solvent, solubilising agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavouring, and perfuming agents, thickening agents, colors, viscosity regulators, stabilizes or osmo-regulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and arachis oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, an inventive RNAi agent or micro-RNA inhibitor may be mixed with at least one inert, pharmaceutically acceptable excipient or carrier such as sodium citrate or dicalcium phosphate and one or more of: (a) fillers or extenders such as starches, lactose, sucrose, glucose, mannital, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulphate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

Solid compositions of a similar type may also be employed as fillers in soft and hard-filled gelatine capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferably, in a certain part of the intestinal tract, optionally, in a delaying manner. Examples of embedding compositions which can be used include polymeric substances and waxes.

In certain embodiments, it may be desirable to administer an inventive composition locally to an area in need of treatment. This may be achieved, for example, and not by way of limitation, by local infusion during surgery, topical application, by injection, by means of a catheter, by means of suppository, or by means of a skin patch or stent or other implant.

For topical administration, the composition is preferably formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurat (5%) in water, or sodium lauryl sulphate (5%) in water. Other materials such as antioxidants, humectants, viscosity stabilizers, and similar agents may be added as necessary.

In addition, in certain instances, it is expected that the inventive compositions may be disposed within transdermal devices placed upon, in, or under the skin. Such devices include patches, implants, and injections which release the active ingredient by either passive or active release mechanisms. Transdermal administrations include all administration across the surface of the body and the inner linings of bodily passage including epithelial and mucosal tissues. Such administrations may be carried out using the present compositions in lotions, creams, foams, patches, suspensions, solutions, and suppositories (rectal and vaginal).

Transdermal administration may be accomplished through the use of a transdermal patch containing an active ingredient (i.e., the RNAi agent or micro-RNA inhibitor) and a carrier that is non-toxic to the skin, and allows the delivery of the ingredient for systemic absorption into the bloodstream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may be suitable. A variety of occlusive devices may be used to release the active ingredient into the bloodstream such as a semi-permeable membrane covering a reservoir containing the active ingredient with or without a carrier, or a matrix containing the active ingredient.

Suppository formulations may be made from traditional materials, including cocoa butter, with or without the addition of waxes to alter the suppository's melting point, and glycerine. Water soluble suppository bases, such as polyethylene glycols of various molecular weights, may also be used.

Materials and methods for producing various formulations are known in the art and may be adapted for practicing the subject invention. Suitable formulations for the delivery of antibodies can be found, for example, in "Remington's Pharmaceutical Sciences", E. W. Martin, $18^{th}$ Ed., 1990, Mack Publishing Co.: Easton, Pa.

B. Additional Biologically Active Agents

In certain embodiments, a RNAi agent or micro-RNA inhibitor, is the only active ingredient in a pharmaceutical composition of the present invention. In other embodiments, the pharmaceutical composition further comprises one or more biologically active agents. Examples of suitable biologically active agents include, but are not limited to, anti-inflammatory agents, immunomodulatory agents, analgesics, antimicrobial agents, antibacterial agents, antibiotics, antioxidants, antiseptic agents, and combinations thereof.

In such pharmaceutical compositions, the RNAi agent or micro-RNA inhibitor and the at least one additional therapeutic agent may be combined in one or more preparations for simultaneous, separate or sequential administration of the RNAi agent or micro-RNA inhibitor and therapeutic agent(s). More specifically, an inventive composition may be formulated in such a way that the RNAi agent or micro-RNA inhibitor and therapeutic agent(s) can be administered together or independently from each other. For example, the RNAi agent or micro-RNA inhibitor and therapeutic agent can be formulated together in a single composition. Alternatively, they may be maintained (e.g., in different compositions and/or containers) and administered separately.

III—Identification of Melanoma Patients Therapeutically Responsive to Treatment Targeting TYRP1 RNA Transcript The invention provides a method of predicting whether or not a subject suffering from melanoma will receive a clinical benefit against the disease by receiving therapeutic treatment targeting TYRP1 RNA transcript (mRNA or circRNA). The method is used to determine whether or not the melanoma in the patient will be therapeutically responsive to a therapeutic treatment targeting TYRP1 RNA transcript (mRNA or circRNA). In other words, the method is used to determine the probability of therapeutic response in the melanoma patient following administration of a therapeutic treatment targeting TYRP1 RNA transcript (mRNA or circRNA).

In general, a biological sample is obtained from the melanoma patient, and the amount of miR-155 present in the sample is determined, and compared to the amount of miR-155 measured in a biological sample obtained from a healthy subject (or a cohort of healthy subjects) and/or to the amount of miR-155 measured in a biological sample obtained from a control patient diagnosed with non-metastatic melanoma (or a cohort of control patients diagnosed with non-metastatic melanoma) and/or to the amount of miR-155 measured in a biological sample obtained from a control patient diagnosed with metastatic melanoma (or a cohort of control patients diagnosed with metastatic melanoma). The melanoma patient is identified as therapeutically responsive to a treatment targeting TYRP1 RNA transcript if the amount of miR-155 measured in the biological sample obtained from the melanoma patient is lower than the amount of miR-155 measured in the biological sample obtained from the healthy subject (or a cohort of healthy subjects). Alternatively or additionally, the melanoma patient is identified as therapeutically responsive to a treatment targeting TYRP1 RNA transcript if the amount of miR-155 measured in the biological sample obtained from the melanoma patient is lower than the amount of miR-155 measured in the biological sample obtained from the control patient diagnosed with non-metastatic melanoma (or a cohort of control patients diagnosed with non-metastatic melanoma).

In certain embodiments, the amount of miR-16 is determined instead of miR-155. In other embodiments, the level of miR-155 and the level of miR-16 are determined.

In certain embodiments, a further step is performed. A biological sample is obtained from the melanoma patient, and the amount of TYRP1 mRNA or circRNA and/or the amount of MITF mRNA or circRNA and/or the amount of RAB17 mRNA or cirRNA present in the sample is determined, and compared to the amount of TYRP1 mRNA or circRNA or to the amount of MITF mRNA or circRNA or to the amount of RAB17 mRNA or circRNA, respectively, measured in a biological sample obtained from a healthy subject (or a cohort of healthy subjects) and/or to the amount of TYRP1 mRNA or circRNA or of MITF mRNA or circRNA or of RAB17 mRNA or circRNA, respectively, measured in a biological sample obtained from a control patient diagnosed with non-metastatic melanoma (or a cohort of control patients diagnosed with non-metastatic melanoma) and/or to the amount of TYRP1 mRNA or circRNA or of MITF mRNA or circRNA or to the amount of RAB17 mRNA or circRNA, respectively, measured in a biological sample obtained from a control patient diagnosed with metastatic melanoma (or a cohort of control patients diagnosed with metastatic melanoma). The melanoma patient is identified as therapeutically responsive to a treatment targeting TYRP1 mRNA or circRNA or of MITF mRNA or circRNA or of RAB17 mRNA or circRNA, respectively, if the amount of TYRP1 mRNA or circRNA or of MITF mRNA or circRNA or of RAB17 mRNA or circRNA, respectively, measured in the biological sample obtained from the melanoma patient is higher than the amount of TYRP1 mRNA or circRNA or of MITF mRNA or circRNA or of RAB17 mRNA or circRNA, respectively, measured in the biological sample obtained from the healthy subject (or a cohort of healthy subjects). Alternatively or additionally, the melanoma patient is identified as therapeutically responsive to a treatment targeting TYRP1 RNA transcript if the amount of TYRP1 mRNA or circRNA or of MITF mRNA or circRNA or of RAB17 mRNA or circRNA, respectively, measured in the biological sample obtained from the melanoma patient is higher than the amount of TYRP1 mRNA or circRNA or of MITF mRNA or circRNA or of RAB17 mRNA or circRNA, respectively, measured in the biological sample obtained from the control patient diagnosed with non-metastatic melanoma (or a cohort of control patients diagnosed with non-metastatic melanoma).

As used herein, the term "MITF" refers to the gene that encodes the transcription factor called microphthalmia-associated transcription factor. More specifically, the term "MITF" refers to the human MITF gene that is located on the short (p) arm of chromosome 3 at position 14.2-14.1. Several isoforms of MITF are known (GenBank Accession Numbers RefSeq(mRNA): NM_000248.3, NM_001184967.1, NM_001184968.1, NM_006722.2, NM_198158.2, NM_198159.2, NM_198177.2, NM_198178.2).

In certain embodiments, a further step is performed. A biological sample is obtained from the melanoma patient, and the haplotype for SNPs rs683 and rs910 of TYRP1 mRNA is determined. The melanoma patient is identified as therapeutically responsive to a treatment targeting TYRP1 mRNA if a haplotype A/C is determined for the melanoma patient.

In certain preferred embodiments, a method for predicting whether a melanoma patient is potentially therapeutically responsive to a treatment targeting TYRP1 RNA transcription comprises measuring the levels of miR-155 and/or of miR-16, of TYRP1 mRNA or circRNA, of MITF mRNA or circRNA, and of RAB17 mRNA or circRNA and determining the haplotype for SNPs rs683 and rs910 of TYRP1 RNA. The results of such a method may, in particular, be compared to the results obtained for a biological sample obtained from a control patient diagnosed with metastatic melanoma (or a cohort of control patients diagnosed with metastatic melanoma).

In certain embodiments, a further step is performed which comprises administering to the melanoma patient a treatment targeting TYRP1 RNA transcript if the melanoma patient has been identified as therapeutically responsive to a treatment targeting TYRP1 RNA transcript. The treatment targeting TYRP1 RNA transcript may be any one of the methods described herein including: direct silencing of TYRP1 by RNA interference, use of miR-155 inhibitors, miR-133 inhibitors, miR-197 inhibitors and/or miR-330 inhibitors and/or miR-16 inhibitors (in particular miR-155, miR-133, miR-197 and/or miR-330 target site blockers and/or miR-16 target site blockers), and personalized miR-155 approach.

Biological Samples

The methods described herein may be applied to the testing of any biological sample allowing miR-155 and/or miR-16 to be assayed, or allowing TYRP1 RNA transcript or MITF RNA transcript to be assayed or TYRP1 mRNA haplotype to be determined.

Thus, in certain embodiments, the method is performed on a sample obtained from a primary tumor (e.g., cutaneous primary tumor) or from metastases (e.g., cutaneous metastases and/or lymph nodes metastases). The biological sample obtained from the non-metastatic melanoma patient or pool of non-metastatic melanoma patients may be from a primary tumor (e.g., cutaneous primary tumor). Preferably, the biological sample obtained from the healthy subject or pool of healthy subjects is a primary culture of melanocytes (e.g., from a skin sample).

In certain embodiments, the inventive methods are performed on the biological sample without any major manipulation of the sample. In other embodiments, the inventive methods are performed on nucleic acid extracts prepared from the biological sample.

For example, RNA may be extracted from tissue samples and analyzed using a method of the invention. Methods of RNA extraction are well known in the art (see, for example, J. Sambrook et al., *Molecular Cloning: A Laboratory Manual*, 1989, $2^{nd}$ Ed., Cold Spring Harbour Laboratory Press: New York). Most methods of RNA isolation from bodily fluids or tissues are based on the disruption of the tissue in the presence of protein denaturants to quickly and effectively inactivate RNases. Generally, RNA isolation reagents comprise, among other components, guanidium thiocyanate and/or beta-mercaptoethanol, which are known to act as RNase inhibitors. Isolated total RNA may then be further purified from the protein contaminants and concentrated by selective ethanol precipitations, phenol/chloroform extractions followed by isopropanol precipitation (see, for example, P. Chomczynski and N. Sacchi, Anal. Biochem., 1987, 162: 156-159) or cesium chloride, lithium chloride or cesium trifluoroacetate gradient centrifugations.

Numerous different and versatile kits can be used to extract RNA (i.e., total RNA or mRNA) from human bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Giagen, Inc. (Valencia, Calif.). User Guides that describe in great detail the protocol to be followed are usually included in all these kits. Sensitivity, processing time and cost may be different from one kit to another. One of ordinary skill in the art can easily select the kit(s) most appropriate for a particular situation.

In certain embodiments, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "*Molecular Cloning: A Laboratory Manual*", 1989, $2^{nd}$ Ed., Cold Spring Harbour Laboratory Press: New York; "*Short Protocols in Molecular Biology*", F. M. Ausubel (Ed.), 2002, $5^{th}$ Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each genetic probe being monitored, or using thermostable DNA polymerases (such as avian myeloblastosis virus reverse transcriptase or Moloney murine leukemia virus reverse transcriptase).

In certain embodiments, RNA extraction is not required, for example when miRNA quantification is carried out using the Nanostring technology that only requires cell lysate.

Determination of miR-155 or miR-16 Levels

The determination of miR-155 or miR-16 levels in biological samples (from the melanoma patient and from the healthy subject or other control patients) may be performed using any suitable method known in the art. The expression profiles of many different miRNAs in parallel can be measured by microarray analysis or deep sequencing (e.g., Genome Analyzer or Genome Sequencer FLX), wherein Northern blotting, real-time RT-PCR (e.g., TaqMan PCR), Nanostring technology and in situ hybridization (e.g., QuantiGene 2.0 miRNA) can be used to determine the level of individual miRNAs.

Determination of TYRP1 (and/or MITF and/or RAB17) RNA Transcript Levels

The determination of TYRP1 (and/or MITF and/or RAB17) mRNA or circRNA levels in biological samples (from the melanoma patient and from the healthy subject) may be performed using any suitable method known in the art.

Nucleic acid-based techniques for assessing expression are well known in the art. Isolated mRNA can be used in hybridization or amplification assays that include, but are not limited to, Southern or northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length, preferably between 15 and 40 nucleotides in length, and sufficient to specifically hybridize under stringent conditions to an mRNA or genomic DNA encoding TYRP1.

A nucleic acid probe may be labeled with a detectable moiety. The association between the nucleic acid probe and detectable moiety can be covalent or non-covalent. Detectable moieties can be attached directly to the nucleic acid probes or indirectly through a linker (E. S. Mansfield et al., Mol. Cell. Probes, 1995, 9: 145-156). Methods for labeling nucleic acid molecules are well-known in the art (for a review of labeling protocols, and label detection techniques, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153).

Determination of TYRP1 Haplotype

The determination of the allelic forms of SNPs rs683 and rs910 of TYRP1 RNA transcript using a biological sample obtained from the melanoma patient may be performed using any suitable method known in the art. For example, SNPs may be determined using hybridization-based methods (such as dynamic allele-specific hybridization, allele Specific Oligonucleotide hybridization, use of molecular beacons, or SNP microarrays), enzyme-based methods, restriction fragment length polymorphism (RFLP), PCR-based methods, or sequencing.

Uses of the Inventive Method

Using the results obtained by a method according to the present invention (i.e., whether the melanoma of a patient is a potentially aggressive melanoma that would benefit from a treatment targeting TYRP1 RNA transcript), skilled physicians may individualize melanoma therapy. Selection of an appropriate therapeutic regimen for a given melanoma patient may be made based solely on the results obtained using a method of the invention. Alternatively, the physician may also consider other clinical or pathological parameters and/or take into account results from other tests such as histopathological criteria described in the American Joint Committee on Cancer (AJCC) melanoma staging system.

A method according to the invention may also be used to assess to monitor the efficacy of a therapeutic treatment targeting TYRP1 RNA transcript (as defined above). Based on the results obtained in a monitoring assay of the invention, a physician may adjust or optimize the dose of RNAi agent or micro-RNA inhibitor (in particular miR-155 inhibitor, e.g. miR-155 target site blocker) administered to the patient tested in order to achieve therapeutic efficacy and/or to reduce side effects. Alternatively, based on the results obtained in a monitoring assay of the invention, a physician may decide to stop administration of the RNAi agent or micro-RNA inhibitor.

Accordingly, in certain embodiments, the methods of the invention further comprise a step of increasing the dose of RNAi agent or micro-RNA inhibitor administered to the patient. In other embodiments, the methods of the invention further comprise a step of decreasing the dose of RNAi agent or micro-RNA inhibitor administered to the patient. In yet other embodiments, the methods of the invention further comprise a step of stopping administration of the RNAi agent or micro-RNA inhibitor.

The invention will be further illustrated by the following figures and examples. However, these examples and figures should not be interpreted in any way as limiting the scope of the present invention.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data are actually obtained.

Example 1

TYRP1 Governs Melanoma Aggressiveness

Materials and Methods

Plasmids, siRNA and miRNA. Luciferase reporter plasmids (pMIR-REPORT Luciferase (Ambion®) containing 3'UTRs and control sequence) were kindly provided by Jingjing Li, University of Toronto. pLightSwitch plasmids (empty or encoding the 3'UTR of Rab17) were purchased in switchgear genomics (Ozyme, France). MicroRNA were purchased from Dharmacon (Themofisher) and siRNA from Sigma-Genosys (St Louis, Mo.) and transfected using Lipofectamine 2000 (Invitrogen, Paisley, UK), following manufacturer's instructions.

Cell Lines and Culture Conditions. Metastatic cell lines were derived from metastatic melanoma tumors by the Dermato-Oncology Department of Nantes University Hospital and by the Laboratory of Oncology and Experimental Surgery (Prof. G Ghanem) of the Institut Bordet, Brussels.

Cell lines from Nantes were grown in humidified air (37° C., 10% $CO_2$), and in RPMI-1640 medium (Gibco BRL, Invitrogen, Paisley, UK) supplemented with 10% Fetal Bovine Serum (PAA cell culture company, Pasching, Austria) and 1% Penicillin-Streptomycin antibiotics (Gibco BRL, Invitrogen, Paisley, UK). Cells from Brussels were propagated in flasks containing HAM-F10 medium supplemented with 5% heat-inactivated foetal calf serum, 5% heat-inactivated newborn calf serum and with L-glutamine, penicillin and streptomycin at standard concentrations (all from Gibco, Invitrogen, UK).

RNA Reverse Transcription. Total RNAs were extracted from cell samples using Nucleospin RAH kit (Macherey-Nagel, Düren, Germany) and quantified using NanoDrop spectrophotometer ND1000 (Thermo Fisher Scientific, Willington, Del.). Reverse transcription was performed using High capacity cDNA Reverse Transcription kit (Applied Biosystems, Foster City, Calif.). For microRNA quantification, total RNA were extracted from samples using mirVana™ miRNA Isolation Kit (Life technologies, France). Reverse transcription was performed using TAQMAN® MICRORNA RT KIT and MEGAPLEX RT PRIMERS (Life technologies, France).

Relative Quantitative PCR. Quantitative PCR was performed on 25 ng cDNA, in 384-well plates using the SYBR Green™ PCR Master Mix (Applied Biosystems, Foster City, Calif.) with the 7900HT Fast Real-Time PCR System (Applied Biosystems, Foster City, Calif.). Transcript relative amounts were determined using the delta-delta-Ct method, as previously described, and human 18S transcript level or GAPDH was used as internal control for each cell lines samples. S100b was used for samples from tumours (Journe et al., Br. J. Cancer, 2011, 105: 1726-1732). TaqMan assays were performed as recommended by the manufacturer (Life technologies, France).

SNP rs683 and rs910 Genotyping. qPCR reactions were performed in duplicate in 96-well plate using the mix "TaqMan® Universal Master Mix II, No. AmpErase® UNG" (Applied Biosystems), primers and probes were supplied by Applied Biosystems (rs683 and rs910). Amplification was performed on the 7900HT Real-Time PCR System (Applied Biosystems). Sequenced DNA homozygous or heterozygous for the SNP rs683 and rs910 were used as controls for each analysis (3 ng/reaction, NA18486, NA18501, NA18917, Coriell).

RNA Immunoprecipitation. These experiments have been performed in 501Mel cells as previously published.

Luciferase Assay. MicroRNA target validation assays were performed as described below. 501Mel cells were seeded 24 hours before transfection at a density of 40,000 cells/well in 24-well plates. 80 ng of empty pMIR-Reporter vector or pMIR-Reporter 3'UTR was co-transfected with 15 nM miRNA with Lipofectamine 2000 according to manufacturer's instructions. Firefly luciferase activity was normalized to protein content using Bicinchoninic Acid Kit from Sigma-Aldrich®. At 72 hours after transfection, luciferase activities were measured with the dual-luciferase reporter system (Promega) using a luminometer (Centro $XS^3$ LB960, Berthold Technologies).

Tissues. Cutaneous and lymph node metastases (N=192) were collected from patients with stage III and IV melanoma undergoing surgery as a part of the diagnostic work-up or therapeutic strategy at Institut Jules Bordet (Brussels) from 1998 to 2009. Samples were collected randomly with no inclusion or exclusion criteria. Immediately after surgery, specimens were snap-frozen in liquid nitrogen and stored at −80° C. until use. This study was approved by the ethic committee of Institut Jules Bordet. The majority of the melanomas were of superficial spreading or nodular histological subtypes with Breslow thickness >1 mm.

In Silico Analyses. miRNA-binding sites on Rab17 and TYRP1 mRNAs were predicted using web-based programs: TargetScanHuman, microRNA, and DianaTools, which are all available online.

Determination of Melanin Content. The melanin content of melanoma cells was determined by spectrophotometry. Briefly, cells were harvested, washed twice with phosphate-buffered saline, and counted. Melanin was solubilized in 0.2 M NaOH ($10^6$ cells/ml). Melanin concentration was determined by measuring absorbance at 475 nm and comparing with a standard curve of known synthetic melanin concentrations (Sigma). Melanin content is expressed in $\mu g/10^6$ cells.

Western Blot. Harvested cells were solubilized in Laemmli buffer. Resulting protein samples were denatured at 95° C., resolved by SDS-PAGE and transferred onto Hybond™-C Extra nitrocellulose membranes (Amersham Biosciences, Bucks, UK). Membranes were probed with appropriated antibodies and signals were detected using the Fujifilm LAS-3000 Imager (Fuji Photo Film, Tokyo, Japan). Primary antibodies were: anti-TYRP1 (G-17) and anti-Hsc70 (B6) (Santa Cruz Biotechnology, Santa Cruz, Calif.), and anti-Rab17 (N1C3) (GenTex, Tebu-bio), anti-α-Tubulin (B-5-1-2) (Sigma, St Louis, Mo.). Horseradish-Peroxidase-conjugated secondary antibodies were purchased from Jackson ImmunoResearch (Suffolk, UK).

shRNA Experiments. Lentiviral particles carrying shRNA vector targeting human TYRP1 mRNA (SHCLNV-NM_000550 including clone TRCN0000118673) named shTYRP1, were purchased from Sigma-Aldrich, St Louis, Mo. Lentiviral particles carrying scrambled shRNA were kindly gifted by Georges Baffet (Rennes, France). Multiplicity of infection (MOI) was equivalent to 10 for 501Mel cells, and to 5 for ME1402, M234, A375P and SKMel28 cells. After infection, cells were maintained under selection in the presence of puromycin (Invivogen, San Diego, Calif.).

Cell Mobility Assay. $10^5$ cells were seeded on 24-well 8 µm transwell polycarbonate microporous filters (Corning, Corning, N.Y.) in 100 µL serum-free medium. Medium containing 10% FBS was added in the lower chamber. After 24 hours of incubation at 37° C. and 10% $CO_2$, the upper-side cells were removed and the lower-side cells were stained with a solution containing 0.4% Crystal Violet and 20% ethanol. The experiment was performed three times in duplicate, and four fields per insert were photographed with a light videomicroscope. Cells were counted using ImageJ software.

Matrigel Invasion Assay. The protocol was the same as for motility assays but using 24-well BD Matrigel Invasion Chamber Inserts (BD Biosciences, Bedford, Mass.). The experiment was performed three times in duplicate, and five fields per insert were counted.

Proliferation Assays. For each condition, $1.5 \times 10^4$ 501mel cells or $2.5 \times 10^4$ ME1402 cells were plated in three 35 mm-diameter dishes and cultivated in medium with 5% FBS. Every two days after plating, cells were counted using Malassey chambers. Calculation of mean values allowed plotting of growth curves.

Proliferation Index Evaluation. Cells were seeded in 96-well plates ($8 \times 10^3$ cells/well) in complete medium (day −1). One day after plating (day 0), the culture medium was replaced by a fresh one and cells were cultured for 1 (day 1) or 3 additional days (day 3). At the end of culture, medium was removed and cells were gently rinsed with phosphate-buffered saline (PBS), fixed with 1% glutaraldehyde/PBS for 15 minutes and stained with 0.1% crystal violet (w/v in water) for 30 minutes. Cells were distained under running tap water and subsequently lysed with 0.2% Triton X-100 for 90 minutes (v/v in water). The absorbance was measured at 570 nm using a Multiskan EX Microplate Photometer (Thermo Scientific, Courtaboeuf Cedex, France). On each plate, blank wells containing medium alone were used to estimate measure the background. Proliferation index refers to the ratio of absorbance at day 3 over day 1.

Statistics. Statistical comparisons were performed using analysis of variance. Data are presented as mean+/−SD and differences were considered significant at a P value of less than 0.05. Statistical significance between two independent groups of patient samples was examined using the Mann-Whitney test. PFS and OS were estimated using the Kaplan-Meier method. Univariate analyses were performed by Cox regression model to estimate hazard ratios (HR) and 95% confidence intervals (CI). All statistical analyses were performed using SPSS 15.0 Inc. (Chicago, Ill., USA).

Results

Loss of 3'UTR of TYRP1 mRNA Decreases Melanoma Aggressiveness. To investigate the role of TYRP1, lentiviral knock-down of TYRP1 mRNA was performed in human melanoma (FIG. 1). The shTYRP1 cells displayed a decreased cell spreading and thinner dendrites (FIG. 1a), when compared to shCTR cells. In contrast, no modifications were observed when cells are defective for TYRP1 mRNA (M234 and A375P cell lines). The efficient knock-down of TYRP1 (FIG. 1b) was found to be associated with a strong reduction of cell proliferation of 501Mel and ME1402 cell lines (FIG. 1c) without detectable cell death (data not shown). These results are reinforced by the correlation existing between the proliferation index and the TYRP1 mRNA expression level from 20 melanoma cell lines. A low level of TYRP1 is associated with a lower rate of cell proliferation while a higher level of TYRP1 is associated with a higher level of cell proliferation. The decrease in TYRP1 expression by knock-down was also found to reduce cell migration (FIG. 1d) and cell invasion (FIG. 1e). Finally, in nude mice, shTYRP1 knock-down SKMel28 cells induced tumors of smaller size (FIG. 1f) than control cells (shCTR).

Loss of 3'UTR of TYRP1 Induces a miRNA Shifting. Since mRNAs are usually targeted by miRNA, the Applicant explored the possibility that the knock-down of TYRP1 releases miRNA (docked on TYRP1) toward other mRNAs, responsible for melanoma aggressiveness (FIG. 2). It was hypothesized that TYRP1 functions as a natural miRNA sponge. To evaluate the miRNA shifting, a miRNA sensor (3'UTR-TYRP1 coupled to F. luciferase) was co-transfected with siRNA targeting the ORF of TYRP1 (FIG. 2a). This experiment demonstrated that, compared to the 3'UTR control, the loss of the endogenous TYRP1 mRNA by RNAi increased the activity/availability of miRNA able to target 3'UTR. Next, an in silico analysis of this 3'UTR was performed to identify putative miRNA recognition elements (MREs) using on line prediction tools (FIG. 2b). Using bioinformatics tools, it was found that only the miR-330 MRE seems to be conserved across species (data not shown). Two other miRNAs, miR-155 and, were also selected since they were already known to target TYRP1 and 8 other miRNAs were further selected based on their expression levels in 501Mel and SKMel28 cells and based on the literature.

To evaluate the ability of these miRNAs to target TYRP1, miRNA-mimics were transfected in 501Mel cells and the TYRP1 mRNA levels were quantified 3 days post-transfection (FIG. 2c). Only miR-155 and miR-133 were found to be able to significantly decrease TYRP1 mRNA expression. This was confirmed using a luciferase assay (co-transfection of 3'UTR-TYRP1 coupled to F. luciferase and miRNA mimics) (FIG. 2d). At the protein level, only the miR-155 decreased the expression of TYRP1 (FIG. 2e).

Figure 2G:
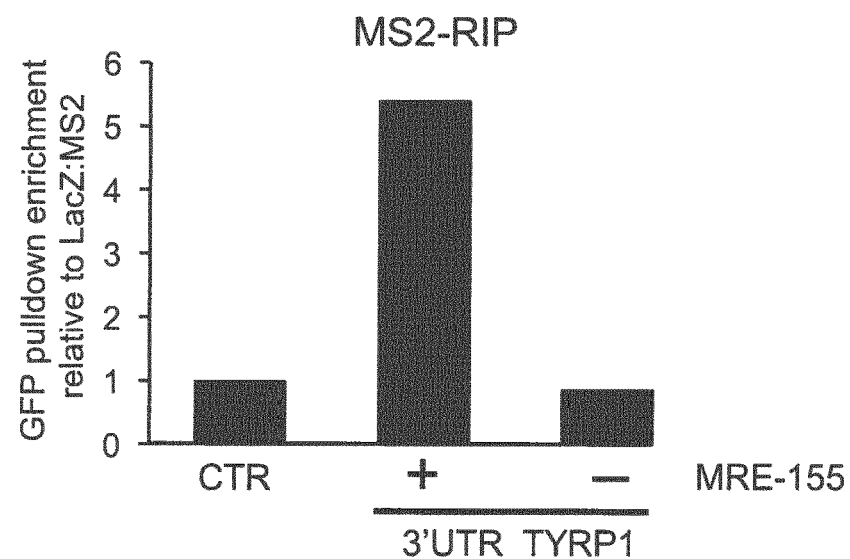
FIG. 2. Loss of 3'UTR of TYRP1 induces a miRNA shifting. (A) miRNA shifting in response to TYRP1 mRNA knock-down. 501Mel cells were co-transfected with siCTR or siTYRP1 (targeting the ORF of TYRP1 mRNA) and miRNA sensor (3'UTR TYRP1 or 3'UTR CTR fused with luciferase reporter). Forty height hours after co-transfection, luciferase assay was performed. The one-tailed Student's t test was used; *p<0.05. (B) In silico analysis of 3'UTR of TYRP1 was performed as explained in the Materials and Methods section of the Examples below, to predict miRNA recognition element. (C) Effect of miRNA mimics on TYRP1 mRNA expression in 501Mel cells. Three days post-transfection, TYRP1 mRNA level was quantified by RT-qPCR. (D) Luciferase assay was performed 48 hours after cotransfection (miRNA mimics and 3'UTR of TYRP1 fused to luciferase reporter) in 501Mel cells. (E) Effect of miRNA mimics on TYRP1 protein expression in 501Mel cells. Hsc70 protein levels are used as loading controls. (F) Direct effect of miR-155 on 3'UTR of wt TYRP1 or mutated for site II and site III (mut) or deleted for the 3 miR-155 recognition elements (MRE-155) on TYRP1 3'UTR (del), which are fused to luciferase reporter. Luciferase assay was performed 48 hours after cotransfection (miR-155 and 3'UTRs of TYRP1 fused to luciferase reporter) in 501Mel cells. (G) RNA immunoprecipitation of 3'UTR of TYRP1 (+) or deleted for 3 MRE-155 (−) or control construct (CTR) fused to MS2 motif (24×). 501Mel cells were co-transfected with a MS2-3'UTR and a plasmid encoding a fusion protein MS2-GFP displaying high affinity for the motif MS2 (24×) of the chimeric RNA (MS2-TYRP1 wt, del or LacZ). RNA Immunoprecipitation was performed using antibody directed against GFP. miRNA associated with chimeric RNA were thus purified. miR-155 associated to chimeric RNA was quantified by TaqMan assay.

Next, the Inventors decided to focus on miR-155. Mutations and deletions of miR-155 MRE ensure a direct effect of miR-155 on TYRP1 3'UTR (FIG. 2f). To definitely prove the binding of miR-155 to TYRP1 3'UTR, RNA immunoprecipitation was performed and purified miRNAs were quantified (FIG. 2g). It was found that miR-155 is immunoprecipitated only in the presence of miR-155 MRE (MRE-155). This demonstrates a direct binding of miR-155 on 3'UTR of TYRP1.

Figure 3:
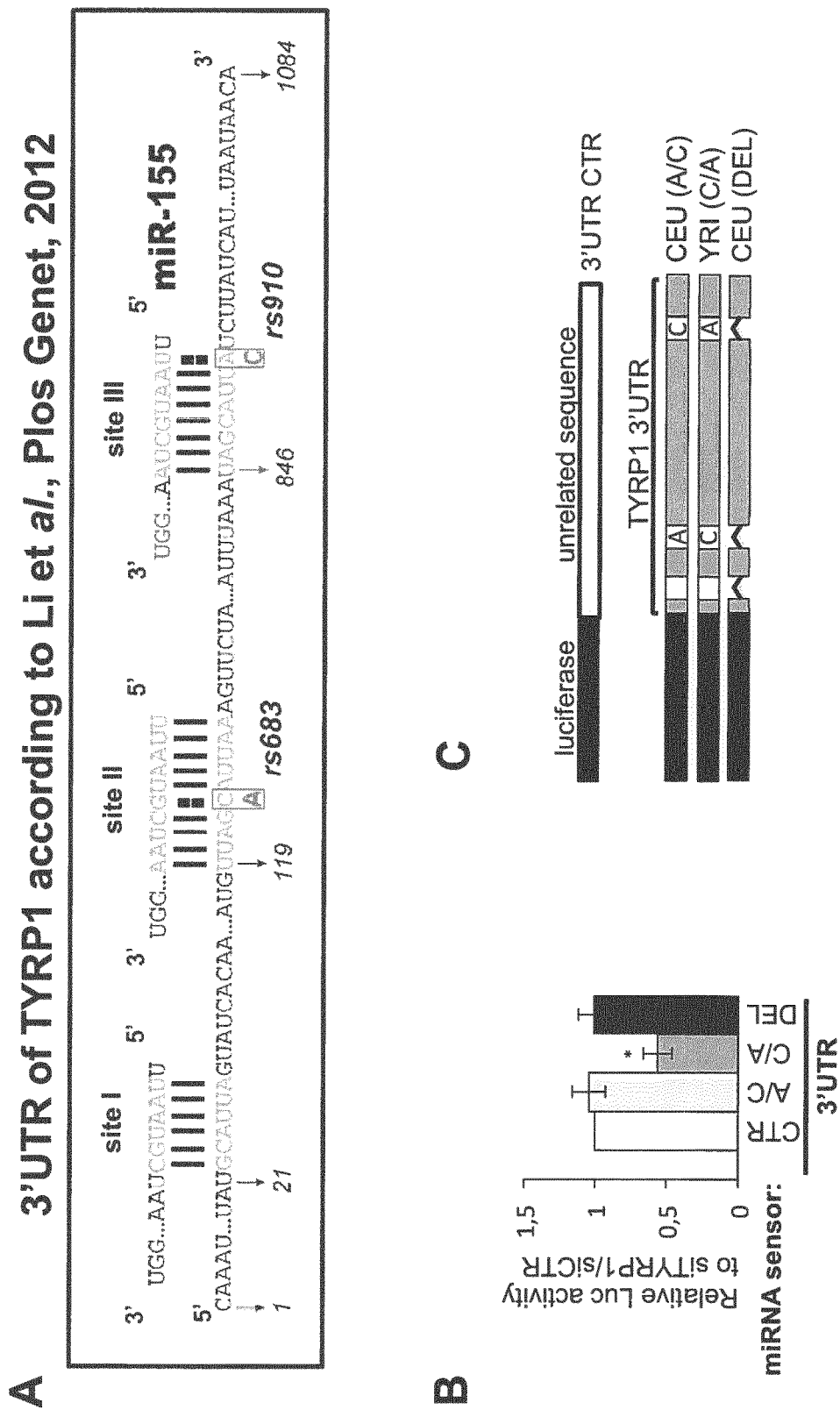
FIG. 3. SNP rs683 and rs910 determine sponge activity of TYRP1 3'UTR. (A) MRE-155 on 3'UTR of TYRP1 mRNA. The 3'UTR of TYRP1 contains three putative miR-155 binding sites, among which two are polymorphic in the HapMap data. Site I is a non-canonical site mediating a 6-mer match to the miRNA seed and is located immediately downstream of the stop codon, while sites II and III mediate canonical pairing with the intact seed region of miR-155. The two SNPs, rs683 and rs910, reside within site II and site III respectively. Two thirds of CEU individuals carry the A/C alleles that alter miRNA-target interaction in contrast to C/A alleles forming intact miRNA sites in CHB, JPT and YRI. Due to their physical proximity, the two SNPs are tightly linked with D'=1 and LOD=24.44, indicating their co-presence (or coabsence) in CEU individuals. (B) miRNA shifting in response to knock-down of TYRP1 mRNA. 501Mel cells, expressing CEU alleles of TYRP1 (A/C), were co-transfected with siCTR or siTYRP1 (targeting the ORF of TYRP1 mRNA) and miRNA sensor (3'UTR TYRP1 A/C (CEU) or C/A (YRI) or Del (MRE-155 deleted) or 3'UTR CTR fused to luciferase reporter). 48 hours after co-transfection, luciferase assay was performed. The one-tailed Student's t test was used; *p<0.05. (C) Luciferase reporter constructs used in B.

SNP rs683 and rs910 Determine Sponge Activity of TYRP1 3'UTR. In theory, the efficiency of a miRNA sponge depends at least on the expression level of the RNA, the number of MRE per molecule and the MRE sequence. Ideally, a miRNA sponge should bind to miRNA but should not be cleaved by this miRNA. The 3'UTR of TYRP1 matches these parameters since (i) TYRP1 is described as the most abundant protein in melanocytes (Tay T et al., 1983), (ii) TYRP1 mRNA is more expressed than GAPDH in a large number of melanoma cell lines (at least in cell lines: 501Mel, SKMel28, and ME1402), and (iii) the 3'UTR of TYRP1 contains three miR-155 MRE (FIG. 3a). Interestingly, it has been reported that SNP rs683 and rs910, which reside in site II and site III of the 3'UTR of TYRP1, respectively (FIG. 3a), affect TYRP1 mRNA decay in response to miR-155 (Li J et al., 2012). Intact MRE-155s are detected in CHB, JPT and YRI (Yoruba in Ibadan, Nigeria (YRI); Japanese in Tokyo, Japan (JPT); Han Chinese in Beijing, China (CHB)), which renders this allele sensible to miR-155. In contrast, two thirds of CEU (Utah residents with ancestry from northern and western Europe) individuals carry the ancestral alleles, strongly limiting the cleavage of TYRP1 3'UTR by miR-155 (this allele corresponds to the construct mut in FIG. 2F).

It is important to keep in mind that CEU individuals are more frequently affected by cutaneous melanoma than JPT or YRI (Armstrong B K & Kricker A., 2001). So the present Applicants investigated if CEU allele of TYRP1 losses the miR-155-target interaction or if CEU TYRP1 3'UTR is able to bind miR-155 without inducing its decay. To do this, the Applicants cell lines and the TYRP1 3'UTR were used, and the Applicants were able to demonstrate in the 501Mel cell line that knock-down of endogenous CEU TYRP1 mRNA induces a miRNA shifting (FIG. 3b) since the miRNA sensor 3'UTR corresponding to the YRI TYRP1 3'UTR was found to be affected. The two other miRNA sensors were not influenced by the miRNA shifting, which demonstrates that (i) the miRNA shifting is limited to miR-155 and (ii) CEU allele of TYRP1 (noted A/C) is resistant to miR-155 activity.

Secondly, SNP rs683 and rs910 determinations were done for the 3'UTR used for the RNA immunoprecipitation performed in FIG. 2g. This 3'UTR corresponds a CEU 3' UTR of TYRP1 (A/C; FIG. 3c). Collectively, these results demonstrated that the 3'UTR of TYRP1 from CEU patients as an efficient miR-155 sponge since it is able to bind and sequester miR-155 in a stoichiometric manner.

TYRP1 3'UTR Shares miRNA with Other mRNAs. Considering the ability of TYRP1 3'UTR to sequester miR-155, the present Applicants hypothesized that natural mRNA targets of miR-155 ought to be down-regulated by miR-155 released from the 3'UTR of TYRP1 knock-down. Among these mRNAs, one or more could direct the melanoma aggressiveness. To identify such mRNAs, transcriptome analyses were performed using two siRNA controls and three individual siRNAs targeting three regions of TYRP1 ORF. These siRNAs were selected because they display different silencing activities (siTYRP1#1<#2<#3) (FIG. 4A). Interestingly, it was found that for the mRNA of the six genes: A2M, MAFF, NRTN, PLA2G6, Rab17 and RasGRP3, the mRNA expression levels are linked to the siRNA efficiencies targeting TYRP1 mRNA (FIG. 4A). Moreover, it was demonstrated that the miR-155 mimic decreased the mRNA expression levels of these genes (FIG. 4B). Several mRNAs are also affected by miR-133, miR-197 and/or miR-330. These results were in harmony with in silico predictions (data not shown).

Next, the Applicants decided to focus on Rab17, a Rab-GTPase that regulates melanocytic filopodia formation and melanosome trafficking (Beaumont K A et al., 2011). Firstly, it was demonstrated, using a luciferase assay, that 3'UTR of Rab17 mRNA is a direct target of miR-7, miR-155, miR-133 and miR-330 probably in a catalytic manner (FIG. 4C). These results were then confirmed at the protein level (FIG. 4D).

Collectively, the data obtained demonstrate that Rab17 mRNA expression level depends at least on miR-155 and miR-133 shared with TYRP1. To further demonstrate this dynamic link, miR-155 sponge (3'UTR of TYRP1 from CEU) or control 3'UTR were transfected and the effects of this transfection were evaluated using a luciferase assay and the following sensor: 3'UTR of Rab17 coupled to R-luciferase (FIG. 4E). The ability of 3'UTR of TYRP1 (CEU) to act as a sponge was thus confirmed. Another indirect proof of the 'miRNA-link' between TYRP1 and Rab17 is the co-expression of these two mRNAs in 193 biopsies of melanoma (FIG. 4F).

Taken together, the results obtained demonstrate that 3'UTR of TYRP1 from CEU patients acts as an efficient 'miR-155 reservoir' that prevents miR-155 from inhibiting other mRNA targets with MRE-155.

Figure 5:
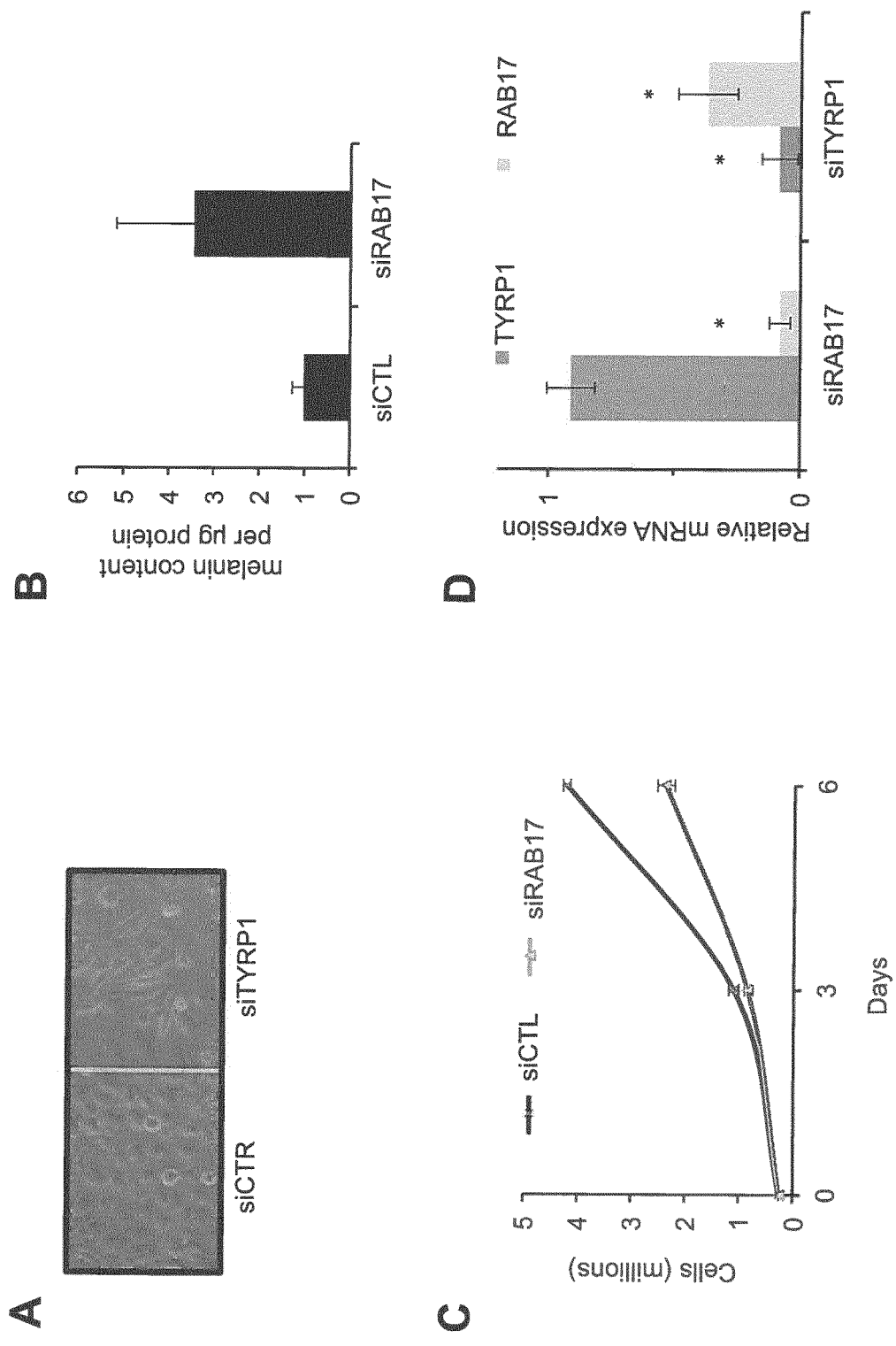
FIG. 5. Rab17 knock-down phenocopies TYRP1 knock-down independently of TYRP1 expression. (A) Phase-contrast images of 501Mel melanoma cells three days post-transfection of siRNA CTR or targeting Rab17 mRNA. (B) Same cells were next analyzed to determine the melanin content per microgram of protein. (C) Proliferation assay on 501Mel cells transfected with siCTR or siRNA targeting Rab17 mRNA. Cells were grown in medium with 10% FBS, and counted every 3 days during 6 days (2 experiments in triplicate). Each point constituting the curves represents the mean of the replicates. (D) Knock-down of Rab17 or TYRP1 in 501Mel cells. Three days post-transfection, mRNA expression levels of Rab17 and TYRP1 were quantified by RT-qPCR. Note that knock-down of Rab17 did not modify TYRP1 expression. The one-tailed Student's t test was used; *p<0.05.

Rab17 Knock-Down Phenocopies TYRP1 Knock-Down Independently of TYRP1 Expression. To identify the molecular mechanism associated with the decrease of melanoma aggressiveness in response to TYRP1 knock-down, a small RNAi screening was performed among mRNA targeted by miR-155 and affected by TYRP1 knock-down (FIG. 5). In other words, the present Applicants looked for the authentic target of miR-155. Surprisingly, the Rab17 knock-down gave a similar phenotype than TYRP1 knock-down did (FIG. 5A). The Applicant confirmed that Rab17 knock-down increased the intracellular accumulation of melanin (FIG. 5B). It is known in the art that Rab17 is implicated in pigmentation through a distal step in the process of melanosome release via filopodia in melanocytes and mouse B16 melanoma cell line (Beaumont K A et al., 2011). As showed in the case TYRP1 KD (FIG. 1), the cell proliferation rate (FIG. 5C) decreased in response to the loss of 85% of Rab17 mRNA expression.

Figure 6:
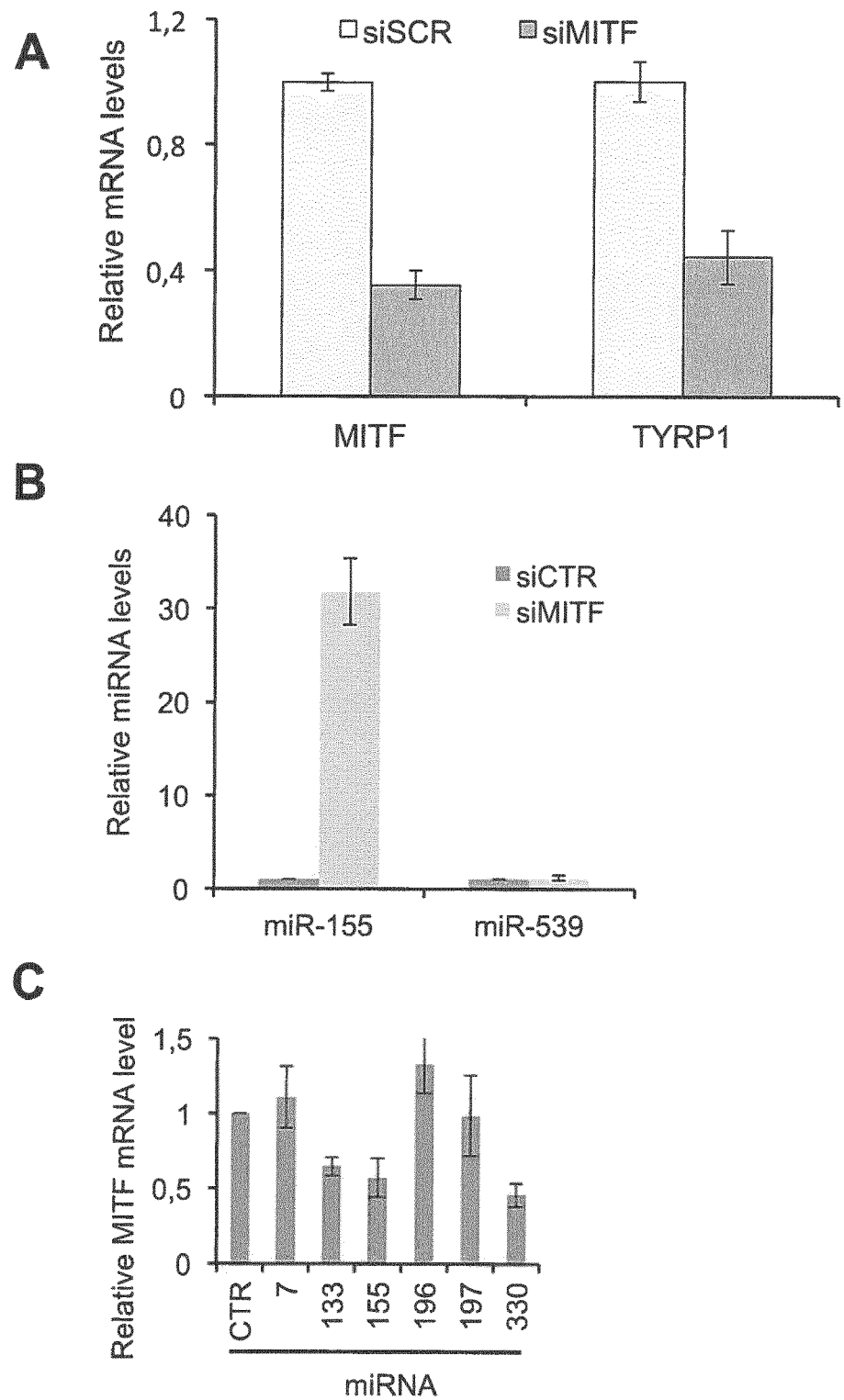
FIG. 6. miR-155 sponge expression level depends on MITF and miR-155. (A) Expression levels of MITF and TYRP1 in response to knock-down of MITF using siRNA (siMITF or siRNA control) in 501Mel cells. RTqPCR were performed three days post-transfection. (B) Quantification of miR-155 and miR-539 expression levels by TaqMan assays three days post-transfection by siCTR or siMITF in 501Mel cells. miR-539 was used as control. (C) Effect of miRNA mimics on MITF mRNA expression in 501Mel cells. Three days post-transfection, MITF mRNA level was quantified by RT-qPCR. The one-tailed Student's t test was used; *p<0.05.
Figure 7A:
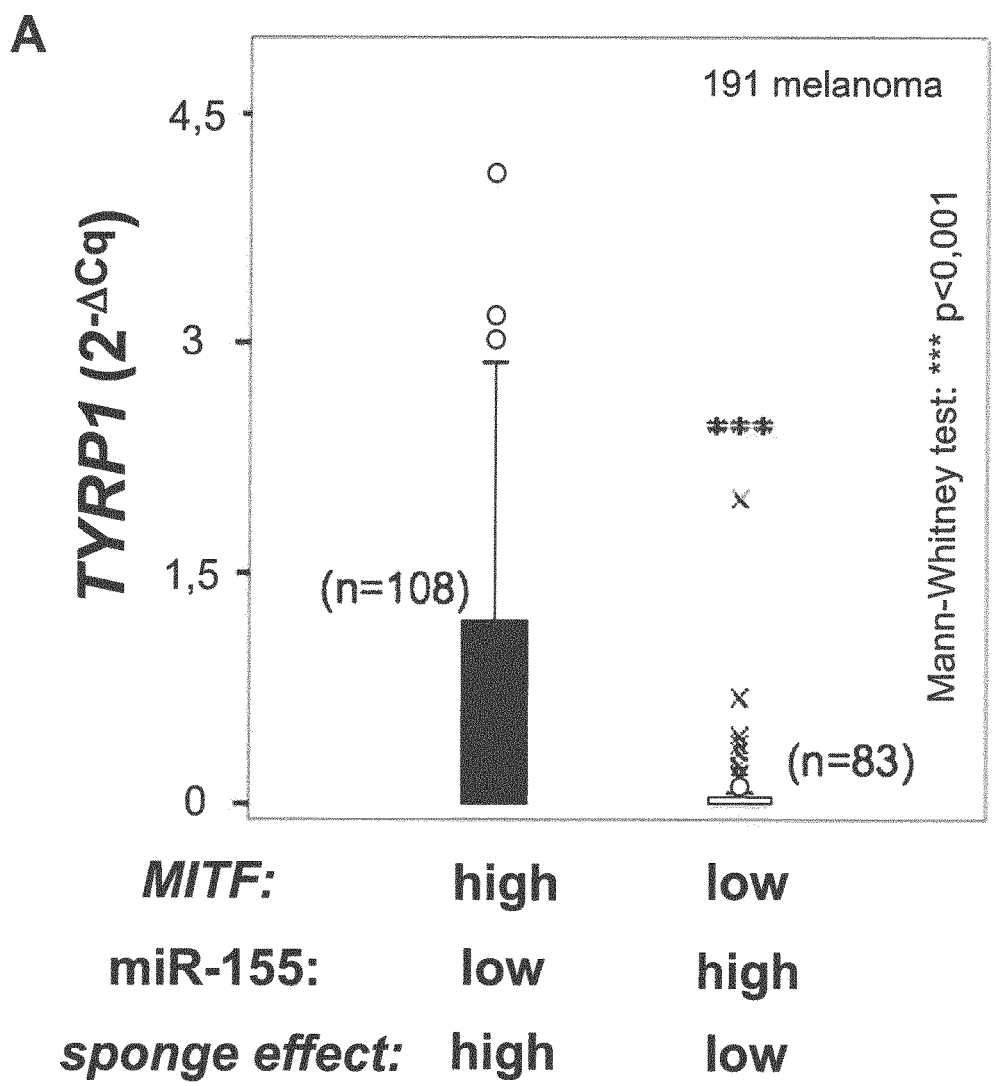
FIG. 7. miR-155 sponge and clinical relevance for metastatic melanoma. (A) Estimation of TYRP1 mRNA level in function of positive and negative regulators of TYRP1 mRNA (respectively, MITF mRNA level and miR-155 level) and TYRP1 sponge effect (depending on SNP rs683 and rs910 located in two miR-155 recognition element of TYRP1 3'UTR). mRNA and microRNA levels have been estimated by, respectively, RT-qPCR and TaqMan assays in 191 tumours. Melanoma tissues were separated in 2 groups. The group of tissues with a high expression of MITF mRNA, a low expression of miR-155 and/or a TYRP1 3'UTR acting as a miR-155 sponge, was significantly associated with a high expression of TYRP1 mRNA, as compared to the rest of tissues (Mann-Whitney test). (B) Description of an arbitrary score combining TYRP1 mRNA, MITF mRNA, miR-155 and sponge effect. Score 0 associated parameters increasing TYRP1 mRNA expression (high synthesis and low degradation), whereas score 1 linked factors decreasing its expression. (C,D) Determination of the progression-free survival (PFS) and overall survival (OS) curves by Kaplan-Meier analysis, according to the score 0/1 calculated in 157 skin and lymph node metastases from melanoma patients. (E,F) Comparison of the prognostic value of the Score versus TYRP1 mRNA expression alone (high/low) or MITF mRNA expression alone (high/low). p-values and hazard ratios were calculated by Cox regressions for each prognostic marker and were compared evaluating progression-free survival and overall survival.

Next, TYRP1 mRNA levels were quantified in response to Rab17 knock-down. Interestingly, the decrease in melanoma aggressiveness obtained in response to Rab17 knock-down did not modify TYRP1 mRNA expression levels (FIG. 5D). Thus, this suggests that TYRP1 mRNA from CEU patient looks like more to miRNA sponge (target mimicry) than ceRNA.

miR-155 Sponge Expression Level Depends on MITF and miR-155. Until now, the Applicants have demonstrated that TYRP1 acts as a miR-155 sponge, preventing the mRNA decay of other mRNA harboring MRE-155 such as Rab17. Next, the Applicants investigated in which conditions a high level of TYRP1 is reached (FIG. 6) since they previously reported that a high expression level of TYRP1 in human melanoma biopsies correlates with a poor clinical outcome. First, they confirmed that MITF drives the transcription of TYRP1 (Hoek K S et al., 2008) since the MITF KD decreased TYRP1 (FIG. 6A). Unexpectedly, miR-155 expression level strongly increased in response to MITF knock-down in contrast to miR-539 (FIG. 6B). Moreover, the Applicants also confirmed that MITF is targeted by miR-155 (FIG. 6C) (Zhang J et al., 2012). Finally, the Applicants propose that, for patients carrying CEU TYRP1 mRNA, miR-155 (sequestered on TYRP1) should not exert an efficient negative feedback loop on MITF. High/aberrant expression level of MITF is already associated with melanoma occurrence (Garraway L A et al., 2005) since MITF drives a large number of genes including Rab17 (Hoek K S et al., 2008).

miR-155 Sponge and Clinical Relevance for Metastatic Melanoma. Next the present Applicants hypothesized that CEU patients harboring miR-155 sponge ought to express a high expression level of both TYRP1 (since it is not cleavable by miR-155) and MITF (since there is no free miR-155), and to exhibit a low level of miR-155 (since MITF represses its expression). For non-Caucasian patients i.e. YRI patients harboring TYRP1 cleavable by miR-155, the opposite situation is expected (i.e., low sponge effect, low MITF, and high miR-155). To test this hypothesis, the Applicants quantified TYRP1, MITF, and miR-155 expression levels and determined SNP rs683 and rs910 in 191 melanoma biopsies. As suspected, the combination (high MITF, low miR-155 and high sponge effect) displayed a higher expression level of TYRP1 mRNA than the other combination (low MITF, high miR-155 and low sponge effect) in 191 melanoma biopsies (FIG. 7a). Hence, the Applicants showed that TYRP1 expression was predicted by a combination of its positive (MITF) and negative (miR155 and SNPs) regulators.

Next, the Applicants tried to improve the prognostic power of TYRP1 by integrating its synthesis (MITF) and degradation (miR-155) regulators into the score calculation used for progression-free survival (PFS) and overall survival (OS) evaluation, regarding to the sponge effect (SNPs). Based on the results obtained in FIG. 7A, the Applicants have calculated two scores. A score 0 was associated with high TYRP1, high MITF, low miR-155 expressions and high sponge effect (low TYRP1 mRNA degradation), while a score 1 was linked to low TYRP1, low MITF, high miR-155 expression and low sponge effects (high TYRP1 mRNA degradation) (FIG. 7B). Using this scoring system in 154 skin and lymph node metastases of stage III and IV melanoma patients, the Applicants clearly showed that score 0 was significantly associated with a shorter PFS (Kaplan-Meier analysis, FIG. 7C) as well as a shorter OS (FIG. 7D). Moreover, they found that the score combining TYRP1, MITF, miR155 and sponge effect had a better prognostic power (higher hazard ratio and lower p-value) than TYRP1 alone or MITF alone for both PFS (Cox regression, FIG. 7E) and OS (FIG. 7F) evaluations, suggesting that it better refined the link between TYRP1 and melanoma progression.

Example 2

TYRP1 Governs Melanoma Aggressiveness

In Example 1, TYRP1 mRNA was demonstrated to act as a miRNA sponge, sequestering miRNAs. miR155 binds TYRP1 3'UTR, being thus titrated out. The knock-down of TYRP1 mRNA renders miR-155 available and released miR-155 can now target other mRNAs leading to a strong reduction of melanoma aggressiveness. Among mRNAs targeted by released miR-155 RAB17 was found to be especially important for melanoma aggressiveness. Silencing RAB17 recapitulates the TYRP1 knock-down phenotype, suggesting that RAB17 may be considered as a critical regulator of melanoma aggressiveness. Quantification of TYRP1 mRNA, MITF mRNA, miR-155 and SNPs rs683 and rs910 was also found to allow to predict: 1) the progression-free survival (PFS) and overall survival (OS) for patients suffering of melanoma and 2) the response to treatment based on TYRP1 mRNA.

The present Example (Example 2) describes results obtained by the inventors, which demonstrate that miR-16 is also sequestered on TYRP1 mRNA. This was established using TYRP1 mRNA immunoprecipitation and miRNA quantification (MS2-RIP as previously described for miR-155) (FIG. 8(A)). In contrast to miR-155, miR-16 was found to increase the levels of both TYRP1 mRNA and protein, suggesting that miR-16 stabilizes TYRP1 mRNA (FIG. 8(B)-(C)).

Figure 8:
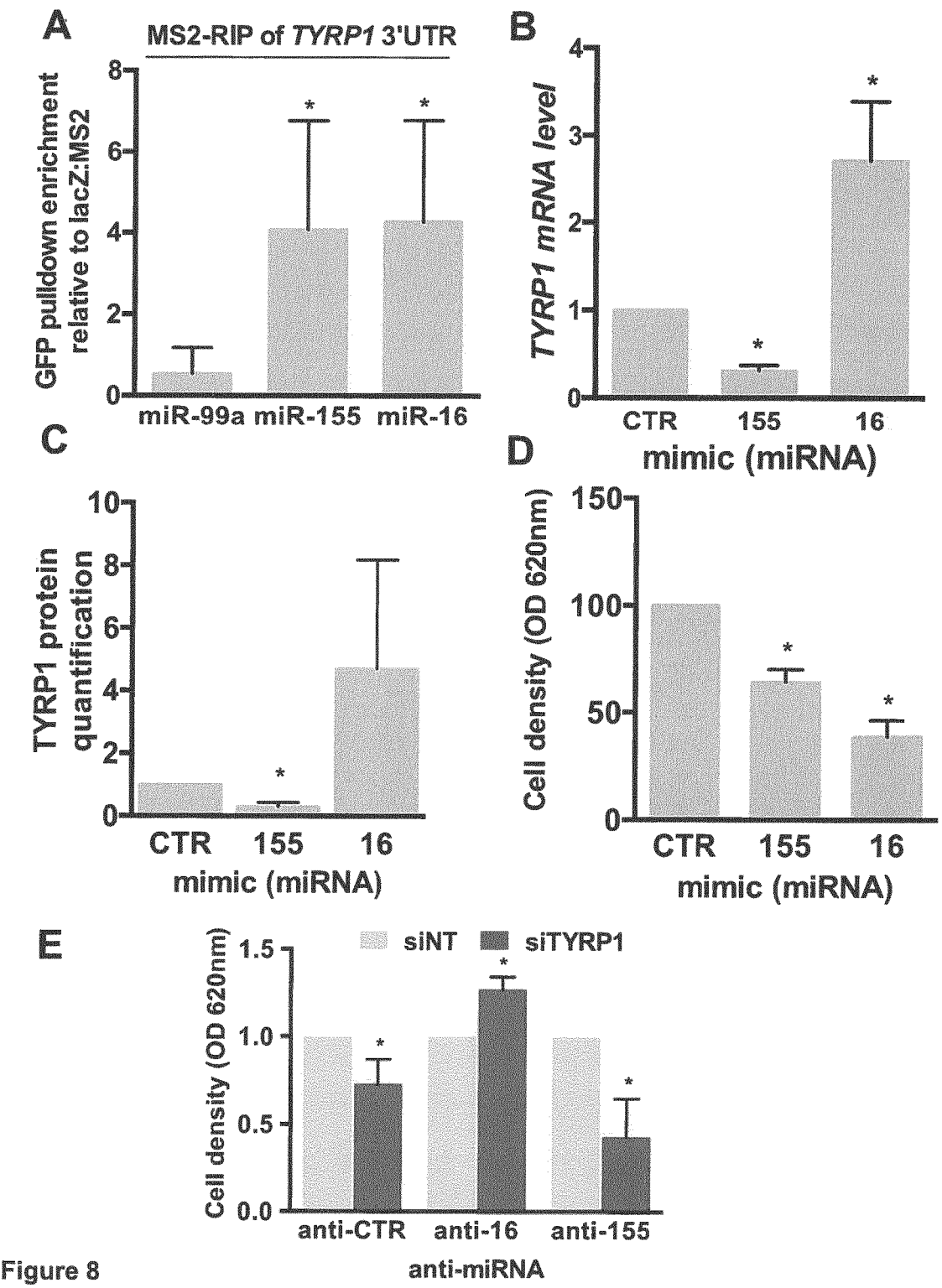
FIG. 8. miR-16 binds to TYRP1 mRNA and regulate melanoma cell proliferation. (A) Binding of miR-16 on TYRP1 mRNA was demonstrated using TYRP1 3'UTR RNA immunoprecipitation followed by quantification of miR-16 assessed by qPCR (MS2-RIP as explained in FIG. 2G). (B) mRNA and (C) protein expression levels of TYRP1 in response to miRNA mimics (miR-155 or miR-16 or miR-CTR) transfection in 501Mel cells. miR-155 strongly reduced TYRP1 expression in contrast to miR-16, which increased the stability of TYRP1 mRNA and consequently increased TYRP1 protein expression in 501Mel cell line. (D) 501Mel cell density in response to miRNA mimics transfection. Three days after transfection, cell density was evaluated by methylene blue coloration followed by its quantification (620 nm). Values obtained for miR-CTR was fixed to 100%. (E) Rescue experiments using anti-miR-16 in response to TYRP1 knock-down. 501Mel cells were co-transfected with siRNA (CTR or targeting TYRP1 mRNA) and anti-miRNA (CTR or anti-16 or anti-155) and cell density was evaluated three days later. siRNA targeting TYRP1 efficiently reduced cell proliferation and this effect was rescued by the anti-miR-16 (in contrast to miR-155). *; p-value<0.05.

Since the inventors have demonstrated that TYRP1 mRNA knock-down release miR-155, reducing cell proliferation by targeting mRNA including RAB17, they evaluated the ability of miR-16 and miR-155 to regulate melanoma cell proliferation (FIG. 8(D)). Interestingly, miR-16 was found to strongly reduce melanoma cell proliferation having a higher impact than miR-155 (FIG. 8(D)).

Next, they investigated the respective weight of endogenous miR-155 and miR-16 in the regulation of cell proliferation by silencing TYRP1 and using parallel anti-miRNA directed against either miR-155 or miR-16 (FIG. 8(E)). Such experiments are called rescue experiments. Anti-miR-16 was found to abolish the decrease of cell proliferation in response to TYRP1 knock-down, while anti-miR-155 did not. Taken together, these results demonstrate that miR-16 can be considered as a miRNA-effector. In other words, TYRP1 knock-down releases miR-16 (and miR-155, both sequestered on TYRP1 mRNA), and miR-16 supports the main anti-melanoma activity by suppressing cell proliferation.

The inventors then identified the miR-16 binding sites (or miRNA recognition elements; MRE-16) on TYRP1 3'UTR in silico (as previously described for miR-155). Three MRE-16 (MRE-16#1 of SEQ ID NO: 9, MRE-16#2 of SEQ ID NO: 10, MRE-16#3 of SEQ ID NO: 11) and three MRE-155 (MRE-155#1 of SEQ ID NO: 6, MRE-155#2 of SEQ ID NO: 7, MRE-155#3 of SEQ ID NO: 8) were identified.

Figure 9:
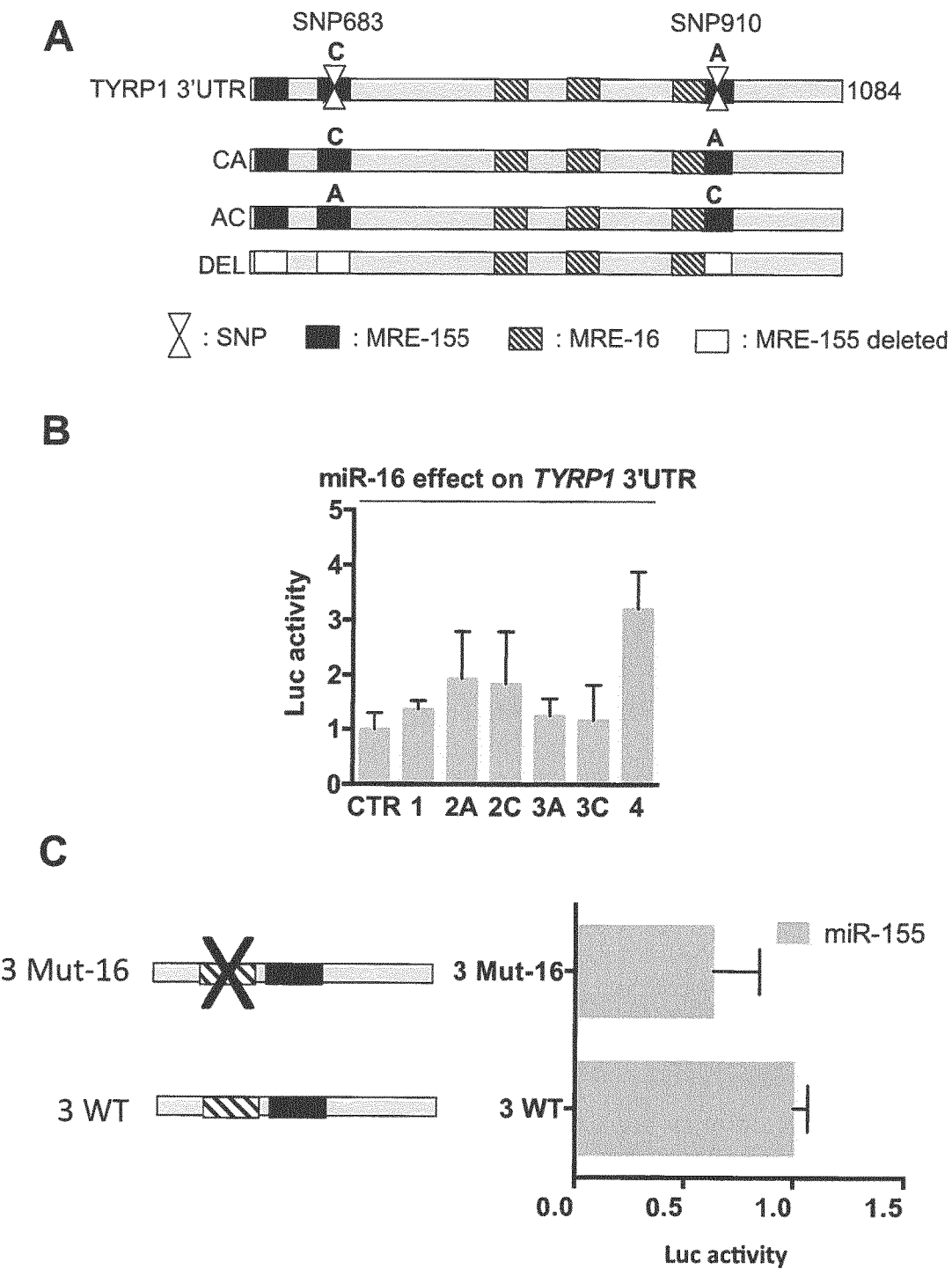
FIG. 9. miR-16 regulates melanoma proliferation by abrogating RAB17 translation. (A) In silico analysis of 3'UTR of TYRP1 was performed as explained in the Materials and Methods section of the Examples, to predict miRNA recognition element. MRE for microRNA Recognition Element and SNP for single nucleotide polyphormism. (B) Short parts of the 3'UTR of TYRP1 were cloned in fusion with the Renilla luciferase gene (named 1, 2A, 2C, 3A, 3C or 4). 501Mel cells were cotransfected with miRNA (CTR or 16) and a plasmid encoding a fusion mRNA (Renilla luciferase in fusion to a part of the 3'UTR of TYRP1 mRNA). Luciferase assay was performed 48 hours after cotransfection. Data are expressed in function of control plasmid (Renilla luciferase) and miRNA CTR. (C) MRE-16#3 reduced miR-155 activity on the third MRE-155 (MRE-155#3). 501Mel cells were cotransfected with miRNA (CTR or 155) and a plasmid encoding a fusion mRNA (Renilla luciferase in fusion to a part of the 3'UTR of TYRP1 mRNA mutated or not for the MRE-16#3). Luciferase assay was performed 48 hours after cotransfection. Data are expressed in function of control plasmid (Renilla luciferase) and miRNA CTR.

Functional studies were performed to understand where miR-16 binds to TYRP1 mRNA using chimeric mRNA (fusion of luciferase and a part of TYRP1 3'UTR) (FIG. 9(A)). The data suggest that miR-16 binds to the construct n° 4 (including two MRE-16) since luciferase activity increased by 3.2-fold in response to miR-16 transfection. The inventors also investigated the role of MRE-16#3 and its relationship with the contiguous MRE-155#3 (FIG. 9(C)). The mutation of MRE-16#3, which abolishes only the binding of miR-16 on this MRE, increased the activity of miR-155 on MRE-155#3. These results strongly suggest that miR-16 limits the activity of miR-155 on MRE-155#3. The present functional studies could explain how miR-16 stabilizes TYRP1 mRNA (FIG. 9(B)) the miR-155 dependent TYRP1 mRNA decay.

Altogether, the data demonstrate that miR-16, sequestered on TYRP1 mRNA, cannot reduce the melanoma cell proliferation. TYRP1 mRNA acts as a miR-16 sponge favoring melanoma aggressiveness. Next, the inventors postulated that miR-16 (released in response to TYRP1 knock-down) could target RAB17 mRNA to limit melanoma cell proliferation. They first confirmed the importance of RAB17 for melanoma cell proliferation in three different cell lines (FIG. 10(A)) using shRNA silencing specifically RAB17. These results were reinforced by in vivo experiments (FIG. 9(B)). SKMel28 cells silenced for RAB17 resulted in smaller tumors than control cells (shRNA CTR) in nude mice.

Figure 10:
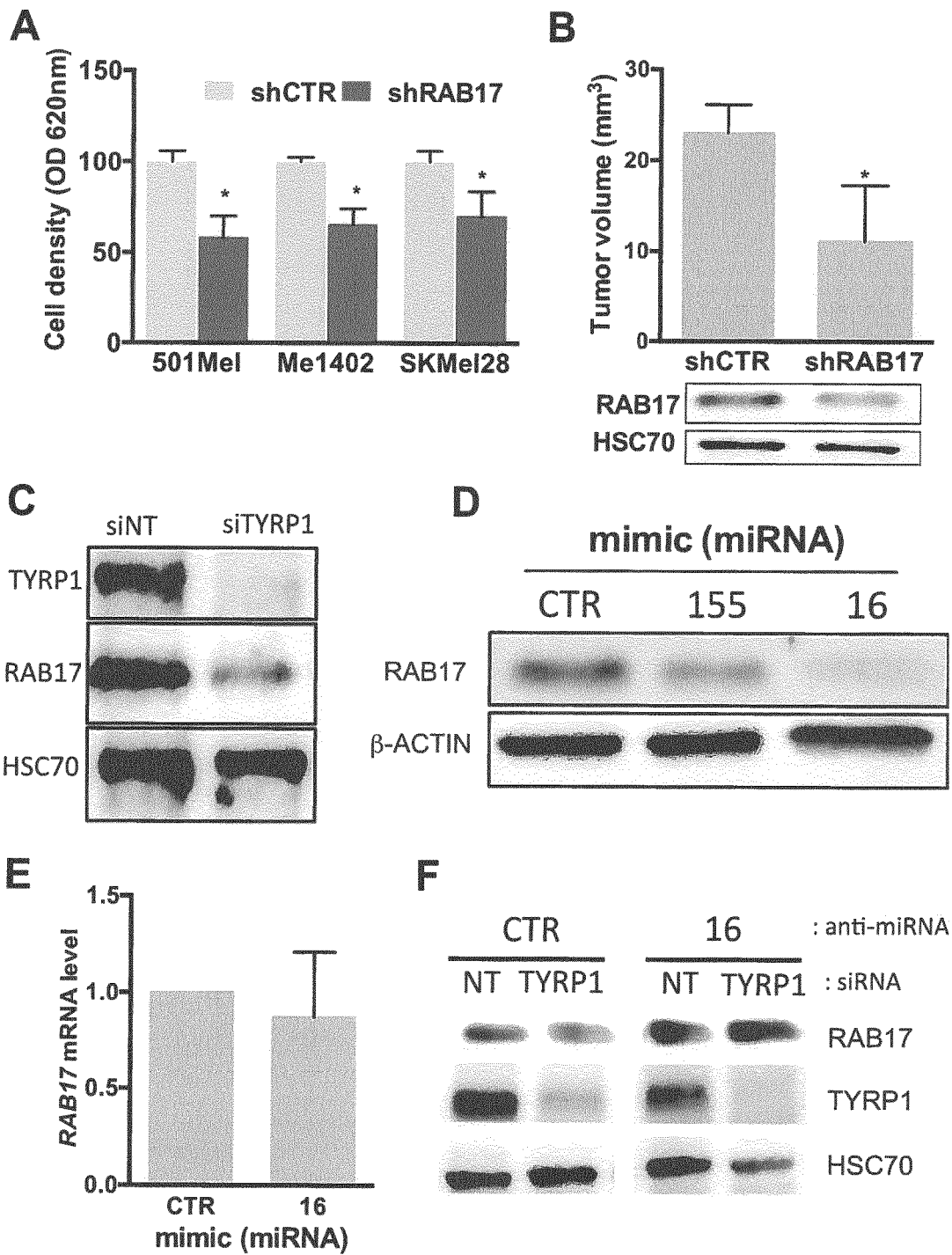
FIG. 10. miR-16 regulates melanoma proliferation by abrogating RAB17 translation. (A) RAB17 knock-out, using shRNA targeting RAB17, significantly reduced cell proliferation in three melanoma cell lines (510Mel, ME1402 and SKMel28). Cell density was evaluated as detailed in FIG. 8(D) and data are expressed in function of shCTR values. (B) Primary tumor growth by $3 \times 10^6$ SKMel28 cells (shCTRL or shRAB17) following subcutaneous injection into nude mice. n=4 or 5 per group. Efficient RAB17 knock-out was illustrated by RAB17 protein expression in response to shRAB17 or shCTR in SKMel28 cell line. Hsc70 protein levels were used as loading controls. (C) TYRP1 knock-down, performed by siRNA, strongly reduced RAB17 protein expression in 501Mel. Three days post-siRNA transfection, TYRP1 and RAB17 protein levels were quantified by western-blot as mentioned in M&M. Hsc70 protein levels are used as loading controls. (D-E) miR-16 abrogated RAB17 translation. (D) mRNA and (E) protein expression levels of RAB17 in response to miRNA mimics (miR-155 or miR-16 or miR-CTR) transfection in 501Mel cells. miR-155 reduced RAB17 protein expression (E) and its mRNA (see FIG. 4A for experimental details). miR-16 abolished RAB17 translation but not RAB17 mRNA expression level. (F) Rescue experiments by anti-miR-16 in response to TYRP1 knock-down. 501Mel cells were co-transfected with siRNA (CTR or targeting TYRP1 mRNA) and anti-miRNA (CTR or anti-16) and RAB17 and TYRP1 protein expression were evaluated three days later by western-blot analyses. siRNA targeting TYRP1 efficiently reduced RAB17 and this effect was rescued by the anti-miR-16.

Then, they demonstrated that TYRP1 knock-down not only abolished TYRP1 expression but also impacted RAB17 protein expression (FIG. 10(A)) in accordance with the effect observed on their mRNA in FIG. 4A. Moreover, they demonstrated that miR-16 strongly reduces RAB17 protein expression (FIG. 10(D)) although miR-16 poorly affected RAB17 mRNA (FIG. 10(E)). Taken together, these results suggest that miR-16, released from TYRP1 3'UTR, is able to reduce cell proliferation by abrogating RAB17 translation. To definitively demonstrate that miR-16 regulates melanoma cell proliferation by abrogating RAB17 translation, rescue experiments were performed using anti-miR-16 or anti-CTR as previously presented in FIG. 8(E). Anti-miR-16 was found to abolish the decrease of RAB17 protein (FIG. 10(F)) in response to TYRP1 knock-down. Thus, anti-miR-16 rescues both RAB17 protein level and cell proliferation (FIG. 8(E)), which strongly suggests that miR-16 supports the main anti-melanoma activity.

Figure 11:
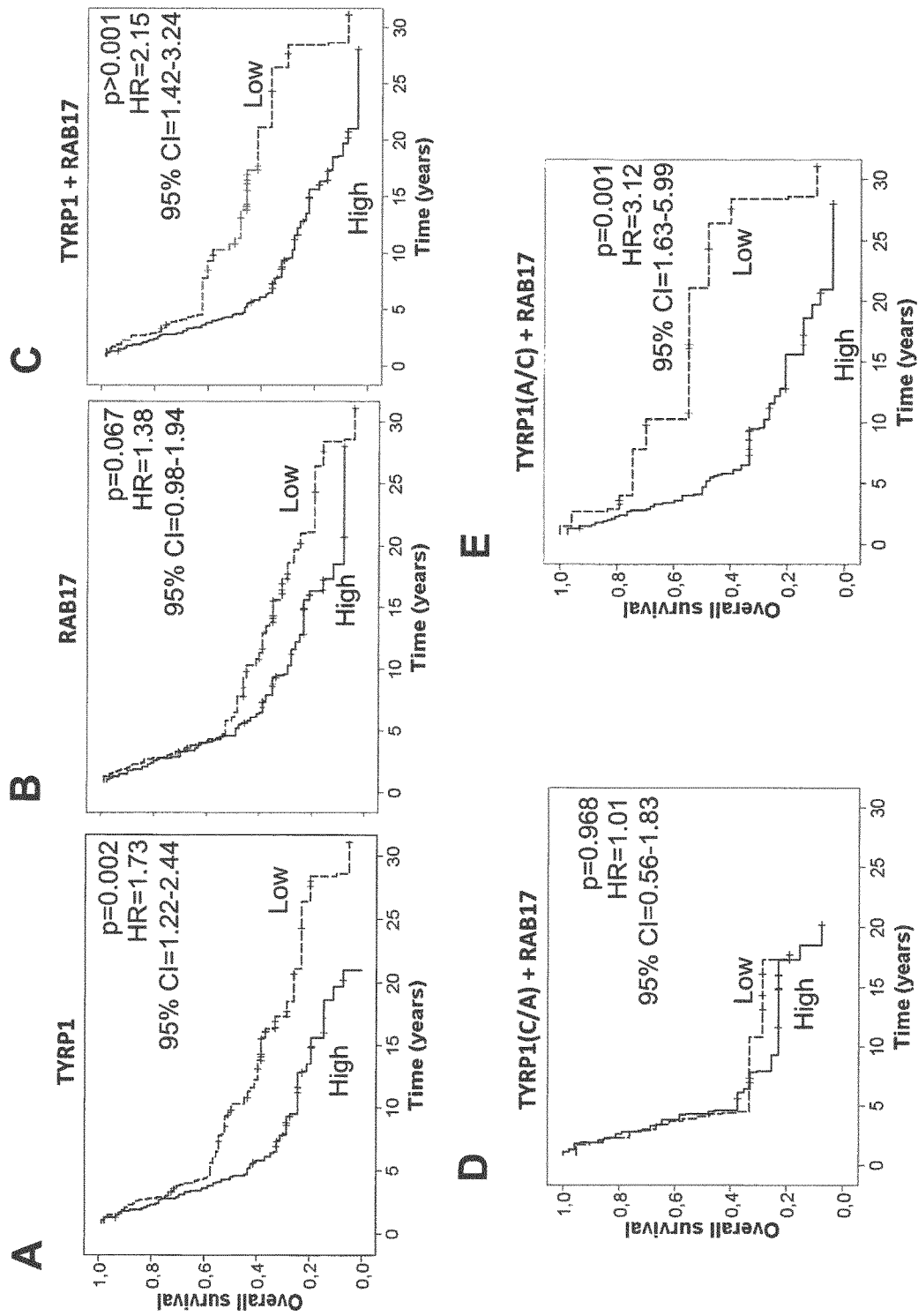
FIG. 11. Clinical relevance of TYRP1 and RAB17 for metastatic melanoma. (A-B) Determination of the overall survival (OS) curves by Kaplan-Meier analysis, according to the expression level of TYRP1 or RAB17 or both mRNA (high or low) calculated in 191 skin and lymph node metastases from melanoma patients. For (C) all patients, (D) patients with TYRP1 C/A genotype for TYRP1 and (E) patients with TYRP1 A/C genotype for TYRP1 (rs638/rs910).

Finally, the inventors aimed at improving the prognostic power of TYRP1 by integrating RAB17 data into the score calculation used for overall survival (OS) (FIG. 11). The determination of the overall survival (OS) curves by Kaplan-Meier analysis, was calculated using the expression level (high or low) of TYRP1 (FIG. 11(A)) or RAB17 alone (FIG. 11(B)) or integrating both TYRP1 and RAB17 data (FIG.

11(C)) from 191 skin and lymph node metastases from melanoma patients. Next, effects of SNP rs683 and rs910 (affecting MRE-155 II and III) have been evaluated on OS (FIG. 11(C-E)). TYRP1 C/A is usually cleaved by miR-155 in contrast to TYRP1 A/C. So, TYRP1 A/C acts as an efficient miRNA sponge in contrast to TYRP1 C/A.

They found that the score combining TYRP1 and RAB17 had a better prognostic power (higher hazard ratio and lower p-value) than TYRP1 alone or RAB17 alone for OS (FIG. 11) evaluation, suggesting that TYRP1 et RAB17 mRNA quantification in melanoma biopsies improves the prognostic value for patients suffering of metastatic melanoma. Moreover, the combination of the SNPs (rs683 & rs910, A/C), TYRP1 and RAB17 levels strongly increased the prognostic power (FIG. 11(E)) compared to (FIG. 11(C)).

Thus, TYRP1 mRNA was demonstrated to act as a miRNA sponge by sequestering miR-155 and miR-16 on its 3'UTR. Such sequestration depends on TYRP1 genotype SNP rs683 and rs910 and miR-16 and miR-155 expression levels. Moreover, expression level of TYRP1 mRNA was also found to correlate with the expression level of MITF, a transcription factor regulating TYRP1 transcription. miR-16 stabilizes TYRP1 mRNA by limiting TYRP1 mRNA decay induced by miR-155. A high expression level of TYRP1 mRNA correlates with a negative prognostic in patients suffering from metastatic melanoma. The present inventors also demonstrated that RAB17, a target of miR-16 and miR-155, governs melanoma cell proliferation. They showed that the score combining TYRP1 and RAB17 mRNA quantification improves the prognostic value for patients suffering of metastatic melanoma.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method for treating melanoma in a subject or for treating, preventing or delaying metastatic melanoma in a subject, comprising a step of administering to said subject a therapeutically effective amount of a micro-RNA inhibitor, wherein the micro-RNA inhibitor is a miR-16 target site blocker that binds to a sequence selected from the group consisting of SEQ ID NO: 9 (AGAAAAUUAAUUAUGUGUAGUUAU), SEQ ID NO: 10 (UGCCUGUGUUUGCCACUGUGUUUCCCUGCC), and SEQ ID NO: 11 (UCCAAUCACUGUGCUU).

2. The method according to claim 1, further comprising a step of administering to said subject a therapeutically effective amount of a miR-155 target site blocker that binds to SEQ ID NO: 8.

3. The method according to claim 2, wherein the miR-155 target site blocker is miR-3123.

* * * * *

SEQUENCE LISTING

<160> NUMBER OF SEQ ID NOS: 11

<210> SEQ ID NO 1
<211> LENGTH: 1084
<212> TYPE: RNA
<213> ORGANISM: Homo sapiens

<400> SEQUENCE: 1

```
caaaugcccu acucucuuau gcauuaguau cacaaaacca ccugguugaa uauaauagau    60
ugaguuauua acuguauuuu cuuucacuuu auuaccuucu uucuaauaca agcauauguu   120
agcauuaaag uucuaggcau acuuuucaaa gcugggaaga cccuuucaga aucuuuucaa   180
uggguuuuaa uuuucaguuc uauuuaaaau ggugaaugac acuaaacucc augauauuua   240
aggauagugu gaagaucuuu ggcaugauuu aaagguugag uaugugaaga uauaaguaag   300
ugaacuacca ugcuuuguuu acguguaaag gaaaauaaug uuugauagua aauguccacu   360
uaaaauacau gaaugggcau uucuaaaaug uuaaaacaua aacacauuuc cauucaugga   420
uauuugucaa cagauuuaaa gaaaaccaca guuauuaauu aaagaaaauu aauuaugugu   480
aguuauaaac caaugaaauu uugauuaacc uuuucaaauu aauguuccag uuugaagacc   540
aaucaaauau auuauuuagu caacauauac uauuuagucu cagguucaag gcuacaacaa   600
aaaucaccau cuuugucaaa cuuuggagag ggaaaaucuu cacuuucuua agcaacaaug   660
gauauugccu guguuugcca cuguguuucc cugccucuca auucgcugaa aaaggaacua   720
ccuauccuua cauuucaccu acuaaugucu cuucuaacau cuuagagguc cauggagaag   780
gcauauggag aacauguuuu auacugcucu auaaauagua uuccaaucac ugugcuuaau   840
uuaaauagca uuaucuuauc auuuaucagc cuuuuaugua uuuuccaagu aaaauauuaa   900
cauauuauuu cauuggucuu cuuuuuuauc ugguucuaua ugaaugcuau uuuuucccuu   960
cucuucuaac augaaauaua uuuucucuuu uugaucuugu gcaugaaac aaucuuccaa  1020
agaacuguau aaggugguca uaagugaaua uuuuaauuaa aauugguaaa aauaaauaau  1080
aaca                                                              1084
```

<210> SEQ ID NO 2
<211> LENGTH: 10
<212> TYPE: RNA
<213> ORGANISM: Homo sapiens

```
<400> SEQUENCE: 2
uuagcauuaa                                                          10

<210> SEQ ID NO 3
<211> LENGTH: 8
<212> TYPE: RNA
<213> ORGANISM: Homo sapiens

<400> SEQUENCE: 3 uagcauua                                                             8

<210> SEQ ID NO 4
<211> LENGTH: 10
<212> TYPE: RNA
<213> ORGANISM: Homo sapiens

<400> SEQUENCE: 4
uuagaauuaa                                                          10

<210> SEQ ID NO 5
<211> LENGTH: 8
<212> TYPE: RNA
<213> ORGANISM: Homo sapiens

<400> SEQUENCE: 5 uagcauuc                                                             8

<210> SEQ ID NO 6
<211> LENGTH: 26
<212> TYPE: RNA
<213> ORGANISM: Homo sapiens

<400> SEQUENCE: 6
gcccuacucu cuuaugcauu aguauc                                        26

<210> SEQ ID NO 7
<211> LENGTH: 37
<212> TYPE: RNA
<213> ORGANISM: Homo sapiens

<400> SEQUENCE: 7
uaccuucuuu cuaauacaag cauauguuag cauuaaa                             37

<210> SEQ ID NO 8
<211> LENGTH: 36
<212> TYPE: RNA
<213> ORGANISM: Homo sapiens

<400> SEQUENCE: 8
uauuccaauc acugugcuua auuuaaauag cauuau                              36

<210> SEQ ID NO 9
<211> LENGTH: 24
<212> TYPE: RNA
<213> ORGANISM: Homo sapiens

<400> SEQUENCE: 9
agaaaauuaa uuauguguag uuau                                          24

<210> SEQ ID NO 10
<211> LENGTH: 30
<212> TYPE: RNA
```

```
<213> ORGANISM: Homo sapiens

<400> SEQUENCE: 10
ugccuguguu ugccacugug uuucccugcc                                    30

<210> SEQ ID NO 11
<211> LENGTH: 16
<212> TYPE: RNA
<213> ORGANISM: Homo sapiens

<400> SEQUENCE: 11
uccaaucacu gugcuu                                                   16
```